(12) United States Patent
Kavazanjian et al.

(10) Patent No.: US 10,724,198 B2
(45) Date of Patent: Jul. 28, 2020

(54) MINERAL PRECIPITATION METHODS

(71) Applicant: Arizona Board of Regents, a body corporate of the State of Arizona acting for and on behalf of Arizona State University, Scottsdale, AZ (US)

(72) Inventors: Edward Kavazanjian, Tempe, AZ (US); Nasser Hamdan, Scottsdale, AZ (US)

(73) Assignee: Arizona Board of Regents, a body corporate of the State of Arizona acting for and on behalf of Arizona State University, Scottsdale, AZ (US)

( * ) Notice: Subject to any disclaimer, the term of this patent is extended or adjusted under 35 U.S.C. 154(b) by 259 days.

(21) Appl. No.: 15/029,866

(22) PCT Filed: Oct. 28, 2014

(86) PCT No.: PCT/US2014/062557
§ 371 (c)(1),
(2) Date: Apr. 15, 2016

(87) PCT Pub. No.: WO2015/065963
PCT Pub. Date: May 7, 2015

(65) Prior Publication Data
US 2016/0244931 A1    Aug. 25, 2016

Related U.S. Application Data

(60) Provisional application No. 61/896,340, filed on Oct. 28, 2013, provisional application No. 61/916,908, filed on Dec. 17, 2013.

(51) Int. Cl.
*E02D 3/12* (2006.01)
*C04B 41/50* (2006.01)
(Continued)

(52) U.S. Cl.
CPC ............... *E02D 3/12* (2013.01); *B09C 1/002* (2013.01); *C01F 11/18* (2013.01); *C02F 1/286* (2013.01);
(Continued)

(58) Field of Classification Search
CPC ................................ E02D 3/12; C04B 41/15
See application file for complete search history.

(56) References Cited

U.S. PATENT DOCUMENTS

| 4,002,204 A | 1/1977 | Cavin et al. |
| 5,143,155 A | 9/1992 | Ferris et al. |

(Continued)

FOREIGN PATENT DOCUMENTS

| JP | 2011157700 | 8/2011 |
| KR | 10-2012-1141978 | 5/2012 |

(Continued)

OTHER PUBLICATIONS

BANG et al., "Application of Novel Biological Technique in Dust Suppression", TRB 2009 Annual Meeting (2009) (Year: 2009).*
(Continued)

*Primary Examiner* — Aileen B Felton
(74) *Attorney, Agent, or Firm* — Snell & Wilmer L.L.P.

(57) ABSTRACT

The present invention provides methods for mineral precipitation of porous particulate starting materials using isolated urease.

13 Claims, 18 Drawing Sheets

Specification includes a Sequence Listing.

(51) Int. Cl.
    C02F 1/42      (2006.01)
    C02F 1/28      (2006.01)
    C02F 1/52      (2006.01)
    C12N 9/78      (2006.01)
    B09C 1/00      (2006.01)
    C01F 11/18     (2006.01)
    C12N 9/80      (2006.01)
(52) U.S. Cl.
    CPC .............. *C02F 1/42* (2013.01); *C02F 1/5236* (2013.01); *C04B 41/50* (2013.01); *C12N 9/78* (2013.01); *C12N 9/80* (2013.01); *C12Y 305/01005* (2013.01); *E02D 2300/0037* (2013.01)

(56) References Cited

U.S. PATENT DOCUMENTS

| | | | |
|---|---|---|---|
| 5,730,873 | A | 3/1998 | Hapka et al. |
| 7,841,804 | B2 | 11/2010 | Ostvold et al. |
| 8,420,362 | B2 | 4/2013 | Crawford et al. |
| 2002/0156337 | A1 | 10/2002 | Jensen et al. |
| 2007/0204990 | A1* | 9/2007 | Kotlar .................. C09K 8/5755 166/276 |
| 2012/0169584 | A1 | 10/2012 | Ostvold |
| 2012/0308306 | A1 | 12/2012 | Kruse |
| 2016/0236949 | A1 | 8/2016 | Sage-Passant |
| 2016/0264463 | A1 | 9/2016 | Dosier et al. |
| 2017/0029689 | A1 | 2/2017 | Wilson et al. |

FOREIGN PATENT DOCUMENTS

| | | |
|---|---|---|
| WO | 1998/000530 | 1/1998 |
| WO | 1999/005394 | 2/1999 |
| WO | 2005/124100 | 12/2005 |
| WO | 2006/066326 | 12/2005 |
| WO | 2007/064213 | 6/2007 |
| WO | 2008/119620 | 9/2008 |
| WO | 2011/078690 | 6/2010 |
| WO | 2013/120847 | 8/2013 |

OTHER PUBLICATIONS

Al Qabany et al., "Microbial Carbonate Precipitation: Correlation of S-Wave Velocity with Calcite Precipitation", Geo-Frontiers, pp. 3993-4001 (2011).
Al Qabany et al., "Factors Affecting Efficiency of Microbially Induced Calcite Precipitation", J. Geotech. Geoenviron. Eng., 138, pp. 992-1001 (2012).
Ozdogan et al., "A study on the triaxial shear behavior and microstructure of biologically treated sand specimens", University of Delaware, (2010).
Bang et al., "Application of Novel Biological Technique in Dust Suppression", TRB 2009 Annual Meeting (2009).
Barksdale et al., "Design, Construction and Testing of Sand Compaction Piles", ASTM Special Technical Publication, pp. 4-18 (1991).
Blakeley et al., "Jack Bean Urease: The First Nickel Enzyme", Journal of Molecular Catalysis, 23, pp. 263-292(1984).
Chou et al., "Biocalcification of Sand through Ureolysis", J. Geotech. Geoenviron. Eng., 137, pp. 1179-1189 (2011).
Das et al., "Purification and characterization of urease from dehusked pigeonpea (*Cajanus cajan* L.) seeds", Phytochemistry, 61, pp. 513-521 (2002).
Dejong et al., Microbially Induced Cementation to Control Sand Response to Undrained Shear, . Geotech. Geoenviron. Eng., 132, pp. 1381-1392 (2006).
Farouz et al., "Evaluation of Axial Capacity of Post Grouted Drilled Shafts", GeoShanghai 2010 International Conference, pp. 216-223 (2010).

Germishuizen et al., "A laboratory study of soil stabilisation with a urea-formaldehyde resin", Journal of the South African Institution of Civil Engineering, 44, pp. 9-12 (2002).
Hamdan et al., "Carbonate Mineral Precipitation for Soil Improvement through Microbial Denitrification", Geo-Frontiers 2011, pp. 3925-3934 (2011).
Hamdan et al., "Sequestration of Radionuclides and Metal Contaminants through Microbially-Induced Carbonate Precipitation", 2011 Pan-Am CGS Geotechnical Conference, (2011).
Harkes et al., "Fixation and distribution of bacterial activity in sand to induce carbonate precipitation for ground reinforcement", Ecological Engineering, 36, pp. 112-117 (2010).
Ivanov et al., "Applications of microorganisms to geotechnical engineering for bioclogging and biocementation of soil in situ", Rev Environ Sci Biotechnol, 7, pp. 139-153 (2008).
Jabri et al., Preliminary crystallographic studies of urease from jack bean and from Klebsiella aerogenes, Journal of Molecular Biology, 227, pp. 934-937 (1992).
King et al., "Post Grouted Drilled Shafts—A Comprehensive Case History from Texas", Contemporary Topics in Deep Foundations, pp. 31-38 (2009).
Marzadori et al., "Immobilization of Jack Bean Urease on Hydroxyapatite: Urease Immobilization in Alkaline Soils", Soil Biology and Biochemistry, 30, pp. 1485-1490 (1998).
Mullins et al., "Predicting End Bearing Capacity of Post-Grouted Drilled Shaft in Cohesionless Soils", Journal of Geotechnical and Geoenvironmental Engineering, 132, pp. 478-487 (2006).
Ng et al., "An Overview of the Factors Affecting Microbial-Induced Calcite Precipitation and its Potential Application in Soil Improvement", World Academy of Science, Engineering and Technology, 62, pp. 723-729 (2012).
Ni et al., "Pervious Concrete Pile: An Innovation Ground Improvement Alternative", Geo-Congress 2013, pp. 2058-2065 (2013).
Pettit et al., "Soil Urease: Activity, Stability and Kinetic Properties", Soil Biology and Biochemistry, 3, pp. 479-484 (1976).
Siddik et al., "Effect of bacterial calcium carbonate precipitation on the geotechnical properties of soils", 2nd International Balkans Conference on Challenges of Civil Engineering, BCCCE, pp. 802-809 (2013).
Sumathi et al., "Impact of indigenous microorganisms on soil microbial and enzyme activities", Scholars Research Library, Archives of Applied Science Research, 4, pp. 1065-1073 (2012).
Van Paassen et al., "Quantifying Biomediated Ground Improvement by Ureolysis: Large-Scale Biogrout Experiment", J. Geotech. Geoenviron. Eng., 136, pp. 1721-1728 (2010).
Whiffin et al., "Microbial Carbonate Precipitation as a Soil Improvement Technique", Geomicrobiology Journal, 24, pp. 417-423 (2007).
International Search Report and Written Opinion for PCT/US2014/062540, dated Feb. 9, 2015.
Hamdan et al., "Carbonate Cementation via Plant Derived Urease", Proceedings of the 18th International Conference on Soil Mechanics and Geotechnical Engineering, Paris 2013.
International Search Report and Written Opinion for PCT/US2014/062557, dated Feb. 12, 2015.
Office Action in U.S. Appl. No. 15/803,700 dated Mar. 1, 2019.
USPTO; Notice of Allowance dated Oct. 23, 2019 in U.S. Appl. No. 15/803,700.
International Search Report and Written Opinion dated Jan. 9, 2020 in PCT/US2019/50474.
Schlumberger, "unconfined compressive strength", Feb. 3, 2017, retrieved on Dec. 16, 2019 from https://web.archive.org/web/20170203220634/https://www.glossary.oilfield.slb.com/en/Terms/u/unconfined_compressive_strength.aspx.
USPTO; Non-Final Office Action dated Dec. 12, 2018 in U.S. Appl. No. 15/029,316.
USPTO; Notice of Allowance dated Jun. 19, 2019 in U.S. Appl. No. 15/029,316.

* cited by examiner

SEQUENCE LISTING

<160> NUMBER OF SEQ ID NOS: 6

<210> SEQ ID NO 1
<211> LENGTH: 840
<212> TYPE: PRT
<213> ORGANISM: Canavalia ensiformis

<400> SEQUENCE: 1

Met Lys Leu Ser Pro Arg Glu Val Glu Lys Leu Gly Leu His Asn Ala
1               5                   10                  15

Gly Tyr Leu Ala Gln Lys Arg Leu Ala Arg Gly Val Arg Leu Asn Tyr
            20                  25                  30

```
Thr Glu Ala Val Ala Leu Ile Ala Ser Gln Ile Met Glu Tyr Ala Arg
         35                  40                  45

Asp Gly Glu Lys Thr Val Ala Gln Leu Met Cys Leu Gly Gln His Leu
 50                  55                  60

Leu Gly Arg Arg Gln Val Leu Pro Ala Val Pro His Leu Leu Asn Ala
 65                  70                  75                  80

Val Gln Val Glu Ala Thr Phe Pro Asp Gly Thr Lys Leu Val Thr Val
                 85                  90                  95

His Asp Pro Ile Ser Arg Glu Asn Gly Glu Leu Gln Glu Ala Leu Phe
                100                 105                 110

Gly Ser Leu Leu Pro Val Pro Ser Leu Asp Lys Phe Ala Glu Thr Lys
             115                 120                 125

Glu Asp Asn Arg Ile Pro Gly Glu Ile Leu Cys Glu Asp Glu Cys Leu
130                 135                 140

Thr Leu Asn Ile Gly Arg Lys Ala Val Ile Leu Lys Val Thr Ser Lys
145                 150                 155                 160

Gly Asp Arg Pro Ile Gln Val Gly Ser His Tyr His Phe Ile Glu Val
                165                 170                 175

Asn Pro Tyr Leu Thr Phe Asp Arg Arg Lys Ala Tyr Gly Met Arg Leu
            180                 185                 190

Asn Ile Ala Ala Gly Thr Ala Val Arg Phe Glu Pro Gly Asp Cys Lys
            195                 200                 205

Ser Val Thr Leu Val Ser Ile Glu Gly Asn Lys Val Ile Arg Gly Gly
            210                 215                 220

Asn Ala Ile Ala Asp Gly Pro Val Asn Glu Thr Asn Leu Glu Ala Ala
225                 230                 235                 240

Met His Ala Val Arg Ser Lys Gly Phe Gly His Glu Glu Lys Asp
                245                 250                 255

Ala Ser Glu Gly Phe Thr Lys Glu Asp Pro Asn Cys Pro Phe Asn Thr
            260                 265                 270

Phe Ile His Arg Lys Glu Tyr Ala Asn Lys Tyr Gly Pro Thr Thr Gly
            275                 280                 285

Asp Lys Ile Arg Leu Gly Asp Thr Asn Leu Leu Ala Glu Ile Glu Lys
290                 295                 300

Asp Tyr Ala Leu Tyr Gly Asp Glu Cys Val Phe Gly Gly Gly Lys Val
305                 310                 315                 320

Ile Arg Asp Gly Met Gly Gln Ser Cys Gly His Pro Pro Ala Ile Ser
                325                 330                 335

Leu Asp Thr Val Ile Thr Asn Ala Val Ile Asp Tyr Thr Gly Ile
            340                 345                 350

Ile Lys Ala Asp Ile Gly Ile Lys Asp Gly Leu Ile Ala Ser Ile Gly
            355                 360                 365

Lys Ala Gly Asn Pro Asp Ile Met Asn Gly Val Phe Ser Asn Met Ile
370                 375                 380

Ile Gly Ala Asn Thr Glu Val Ile Ala Gly Glu Gly Leu Ile Val Thr
385                 390                 395                 400

Ala Gly Ala Ile Asp Cys His Val His Tyr Ile Cys Pro Gln Leu Val
                405                 410                 415

Tyr Glu Ala Ile Ser Ser Gly Ile Thr Thr Leu Val Gly Gly Gly Thr
            420                 425                 430

Gly Pro Ala Ala Gly Thr Arg Ala Thr Thr Cys Thr Pro Ser Pro Thr
            435                 440                 445
```

Gln Met Arg Leu Met Leu Gln Ser Thr Asp Asp Leu Pro Leu Asn Phe
            450                 455                 460

Gly Phe Thr Gly Lys Gly Ser Ser Lys Pro Asp Glu Leu His Glu
465                 470                 475                 480

Ile Ile Lys Ala Gly Ala Met Gly Leu Lys Leu His Glu Asp Trp Gly
                485                 490                 495

Ser Thr Pro Ala Ala Ile Asp Asn Cys Leu Thr Ile Ala Glu His His
            500                 505                 510

Asp Ile Gln Ile Asn Ile His Thr Asp Thr Leu Asn Glu Ala Gly Phe
            515                 520                 525

Val Glu His Ser Ile Ala Ala Phe Lys Gly Arg Thr Ile His Thr Tyr
530                 535                 540

His Ser Glu Gly Ala Gly Gly His Ala Pro Asp Ile Ile Lys Val
545                 550                 555                 560

Cys Gly Ile Lys Asn Val Leu Pro Ser Ser Thr Asn Pro Thr Arg Pro
                565                 570                 575

Leu Thr Ser Asn Thr Ile Asp Glu His Leu Asp Met Leu Met Val Cys
            580                 585                 590

His His Leu Asp Arg Glu Ile Pro Glu Asp Leu Ala Phe Ala His Ser
595                 600                 605

Arg Ile Arg Lys Lys Thr Ile Ala Ala Glu Asp Val Leu Asn Asp Ile
            610                 615                 620

Gly Ala Ile Ser Ile Ile Ser Ser Asp Ser Gln Ala Met Gly Arg Val
625                 630                 635                 640

Gly Glu Val Ile Ser Arg Thr Trp Gln Thr Ala Asp Lys Met Lys Ala
                645                 650                 655

Gln Thr Gly Pro Leu Lys Cys Asp Ser Ser Asp Asn Asp Phe Arg
            660                 665                 670

Ile Arg Arg Tyr Ile Ala Lys Tyr Thr Ile Asn Pro Ala Ile Ala Asn
            675                 680                 685

Gly Phe Ser Gln Tyr Val Gly Ser Val Glu Val Gly Lys Leu Ala Asp
            690                 695                 700

Leu Val Met Trp Lys Pro Ser Phe Phe Gly Thr Lys Pro Glu Met Val
705                 710                 715                 720

Ile Lys Gly Gly Met Val Ala Trp Ala Asp Ile Gly Asp Pro Asn Ala
                725                 730                 735

Ser Ile Pro Thr Pro Glu Pro Val Lys Met Arg Pro Met Tyr Gly Thr
            740                 745                 750

Leu Gly Lys Ala Gly Gly Ala Leu Ser Ile Ala Phe Val Ser Lys Ala
            755                 760                 765

Ala Leu Asp Gln Arg Val Asn Val Leu Tyr Gly Leu Asn Lys Arg Val
770                 775                 780

Glu Ala Val Ser Asn Val Arg Lys Leu Thr Lys Leu Asp Met Lys Leu
785                 790                 795                 800

Asn Asp Ala Leu Pro Glu Ile Thr Val Asp Pro Glu Ser Tyr Thr Val
                805                 810                 815

Lys Ala Asp Gly Lys Leu Leu Cys Val Ser Glu Ala Thr Thr Val Pro
            820                 825                 830

Leu Ser Arg Asn Tyr Phe Leu Phe
            835                 840

<210> SEQ ID NO 2
<211> LENGTH: 837
<212> TYPE: PRT

-continued

<213> ORGANISM: Glycine max

<400> SEQUENCE: 2

```
Met Lys Leu Ser Pro Arg Glu Ile Glu Lys Leu Asp Leu His Asn Ala
1               5                   10                  15
Gly Tyr Leu Ala Gln Lys Arg Leu Ala Arg Gly Leu Arg Leu Asn Tyr
                20                  25                  30
Val Glu Thr Val Ala Leu Ile Ala Thr Gln Ile Leu Glu Phe Val Arg
            35                  40                  45
Asp Gly Glu Lys Thr Val Ala Gln Leu Met Cys Ile Gly Arg Glu Leu
        50                  55                  60
Leu Gly Arg Lys Gln Val Leu Pro Ala Val Pro His Leu Val Glu Ser
65                  70                  75                  80
Val Gln Val Glu Ala Thr Phe Arg Asp Gly Thr Lys Leu Val Thr Ile
                85                  90                  95
His Asp Leu Phe Ala Cys Glu Asn Gly Asn Leu Glu Leu Ala Leu Phe
            100                 105                 110
Gly Ser Phe Leu Pro Val Pro Ser Leu Asp Lys Phe Thr Glu Asn Glu
        115                 120                 125
Glu Asp His Arg Thr Pro Gly Glu Ile Ile Cys Arg Ser Glu Asn Leu
    130                 135                 140
Ile Leu Asn Pro Arg Arg Asn Ala Ile Ile Leu Arg Val Val Asn Lys
145                 150                 155                 160
Gly Asp Arg Pro Ile Gln Val Gly Ser His Tyr His Phe Ile Glu Val
                165                 170                 175
Asn Pro Tyr Leu Thr Phe Asp Arg Arg Lys Ala Tyr Gly Met Arg Leu
            180                 185                 190
Asn Ile Ala Ala Gly Asn Ala Thr Arg Phe Glu Pro Gly Glu Cys Lys
        195                 200                 205
Ser Val Val Leu Val Ser Ile Gly Gly Asn Lys Val Ile Arg Gly Gly
    210                 215                 220
Asn Asn Ile Ala Asp Gly Pro Val Asn Asp Ser Asn Cys Arg Ala Ala
225                 230                 235                 240
Met Lys Ala Val Val Thr Arg Gly Phe Gly His Val Glu Glu Glu Asn
                245                 250                 255
Ala Arg Glu Gly Val Thr Gly Leu Asp Tyr Ser Leu Thr Thr Val Ile
            260                 265                 270
Ser Arg Glu Glu Tyr Ala His Lys Tyr Gly Pro Thr Thr Gly Asp Lys
        275                 280                 285
Ile Arg Leu Gly Asp Thr Asp Leu Phe Ala Glu Ile Glu Lys Asp Phe
    290                 295                 300
Ala Val Tyr Gly Asp Glu Cys Val Phe Gly Gly Gly Lys Val Ile Arg
305                 310                 315                 320
Asp Gly Met Gly Gln Ser Ser Gly His Pro Pro Glu Gly Ser Leu Asp
                325                 330                 335
Thr Val Ile Thr Asn Ala Val Ile Ile Asp Tyr Thr Gly Ile Ile Lys
            340                 345                 350
Ala Asp Ile Gly Ile Lys Asp Gly Leu Ile Ile Ser Thr Gly Lys Ala
        355                 360                 365
Gly Asn Pro Asp Ile Met Asn Asp Val Phe Pro Asn Met Ile Ile Gly
    370                 375                 380
Ala Asn Thr Glu Val Ile Ala Gly Glu Gly Leu Ile Val Thr Ala Gly
385                 390                 395                 400
```

```
Ala Ile Asp Cys His Val His Phe Ile Cys Pro Gln Leu Val Tyr Asp
                405                 410                 415
Ala Val Thr Ser Gly Ile Thr Thr Leu Val Gly Gly Gly Thr Gly Pro
            420                 425                 430
Ala Asp Gly Thr Arg Ala Thr Thr Cys Thr Pro Ala Pro Asn Gln Met
            435                 440                 445
Lys Leu Met Leu Gln Ser Thr Asp Asp Met Pro Leu Asn Phe Gly Phe
450                 455                 460
Thr Gly Lys Gly Asn Ser Ala Lys Pro Asp Glu Leu His Glu Ile Ile
465                 470                 475                 480
Arg Ala Gly Ala Met Gly Leu Lys Leu His Glu Asp Trp Gly Thr Thr
                485                 490                 495
Pro Ala Ala Ile Asp Ser Cys Leu Thr Val Ala Asp Gln Tyr Asp Ile
            500                 505                 510
Gln Val Asn Ile His Thr Asp Thr Leu Asn Glu Ser Gly Phe Val Glu
            515                 520                 525
His Thr Ile Ala Ala Phe Lys Gly Arg Thr Ile His Thr Tyr His Ser
            530                 535                 540
Glu Gly Ala Gly Gly Gly His Ala Pro Asp Ile Ile Lys Val Cys Gly
545                 550                 555                 560
Glu Lys Asn Val Leu Pro Ser Ser Thr Asn Pro Thr Arg Pro Tyr Thr
                565                 570                 575
His Asn Thr Ile Asp Glu His Leu Asp Met Leu Met Val Cys His His
            580                 585                 590
Leu Asn Lys Asn Ile Pro Glu Asp Val Ala Phe Ala Glu Ser Arg Ile
            595                 600                 605
Arg Ala Glu Thr Ile Ala Ala Glu Asp Ile Leu His Asp Lys Gly Ala
            610                 615                 620
Ile Ser Ile Ile Ser Ser Asp Ser Gln Ala Met Gly Arg Ile Gly Glu
625                 630                 635                 640
Val Ile Ser Arg Thr Trp Gln Thr Ala Asp Lys Met Lys Ser Gln Arg
                645                 650                 655
Gly Pro Leu Gln Pro Gly Glu Asp Asn Asp Asn Phe Arg Ile Lys Arg
            660                 665                 670
Tyr Val Ala Lys Tyr Thr Ile Asn Pro Ala Ile Ala Asn Gly Leu Ser
            675                 680                 685
Gln Tyr Val Gly Ser Val Glu Ala Gly Lys Leu Ala Asp Leu Val Leu
            690                 695                 700
Trp Lys Pro Ser Phe Phe Gly Ala Lys Pro Glu Met Val Ile Lys Gly
705                 710                 715                 720
Gly Glu Val Ala Tyr Ala Asn Met Gly Asp Pro Asn Ala Ser Ile Pro
                725                 730                 735
Thr Pro Glu Pro Val Ile Met Arg Pro Met Phe Gly Ala Phe Gly Lys
            740                 745                 750
Ala Gly Ser Ser His Ser Ile Ala Phe Val Ser Lys Ala Ala Leu Asp
            755                 760                 765
Glu Gly Val Lys Ala Ser Tyr Gly Leu Asn Lys Arg Val Glu Ala Val
            770                 775                 780
Lys Asn Val Arg Lys Leu Thr Lys Arg Asp Met Lys Leu Asn Asp Thr
785                 790                 795                 800
Leu Pro Gln Ile Thr Val Asp Pro Glu Thr Tyr Thr Val Thr Ala Asp
                805                 810                 815
Gly Glu Val Leu Thr Cys Thr Ala Ala Lys Thr Val Pro Leu Ser Arg
```

```
                    820                 825                 830

Asn Tyr Phe Leu Phe
            835

<210> SEQ ID NO 3
<211> LENGTH: 838
<212> TYPE: PRT
<213> ORGANISM: Agaricus bisporus

<400> SEQUENCE: 3

Met Arg Leu Leu Pro Arg Glu Glu Ala Lys Val Leu Leu His Gln Val
1               5                   10                  15

Gly Phe Ile Ala Gln Lys Arg Leu Ala Arg Gly Val Lys Leu Asn Lys
            20                  25                  30

Thr Glu Ala Val Ala Leu Ile Ala Ser Val Leu Gln Glu Arg Ile Arg
        35                  40                  45

Asp Gly Arg His Ser Val Ala Glu Leu Met Gln His Gly Lys Lys Ile
    50                  55                  60

Leu Gly Arg Arg His Val Leu Pro Asp Val Pro Ala Leu Leu His Glu
65                  70                  75                  80

Ile Gln Val Glu Gly Thr Phe Leu Asp Gly Val Phe Leu Val Thr Val
                85                  90                  95

His Gln Pro Ile Cys Thr Glu Asp Gly Asp Leu Glu Ala Ala Leu Tyr
            100                 105                 110

Gly Ser Phe Leu Pro Ile Pro Pro Gln Asp Asp Phe Pro Val Ala Pro
        115                 120                 125

Asp Ser Asp Tyr Leu Pro Glu Lys Thr Ala Gly Ala Ile Ile Pro Lys
    130                 135                 140

Gln Glu Asp Ile Val Leu Asn Gln Gly Arg Glu Arg Ile Arg Leu Arg
145                 150                 155                 160

Ile Thr Asn Thr Gly Asp Arg Pro Ile Gln Val Gly Ser His Tyr His
                165                 170                 175

Phe Ile Glu Thr Asn Arg Ala Leu Ser Phe Asp Arg Leu Lys Ser Tyr
            180                 185                 190

Gly Lys Arg Leu Asp Ile Ala Ala Gly Thr Ala Val Arg Phe Glu Pro
        195                 200                 205

Gly Asp Thr Lys Ala Val Thr Leu Val Ser Ile Ser Gly Asn Lys Val
    210                 215                 220

Ile Ser Gly Gly Asn Ser Leu Ala Ser Gly His Ile Gly Thr Phe Arg
225                 230                 235                 240

Ser Glu Val Leu Leu Glu Asp Ile Leu Arg Arg Asp Phe Ala His Val
                245                 250                 255

Ser Glu Pro Gly Ala Leu Glu Val Met Glu Asp Thr Lys Ile Gly Arg
            260                 265                 270

Glu Thr Tyr Ile Ser Met Tyr Gly Pro Thr Val Gly Asp Arg Val Arg
        275                 280                 285

Leu Gly Asp Thr Glu Leu Trp Ile Glu Val Glu His Asp Glu Thr Val
    290                 295                 300

Tyr Gly Asp Glu Val Lys Phe Gly Gly Gly Lys Val Ile Arg Glu Gly
305                 310                 315                 320

Met Gly Gln Ala Thr Asn Arg Ser Ser Asn Glu Thr Leu Asp Leu Val
                325                 330                 335

Ile Thr Asn Ala Leu Ile Val Asp Trp Ser Gly Ile Tyr Lys Ala Asp
            340                 345                 350
```

```
Ile Gly Val Lys Asn Gly Phe Ile Cys Gly Ile Gly Lys Ala Gly Asn
            355                 360                 365

Pro Asp Val Met Ser Asn Ile His Pro Thr Leu Val Ile Gly Ser Ser
370                 375                 380

Thr Glu Val Ile Ala Gly Glu Lys Leu Ile Ile Thr Ala Gly Gly Ile
385                 390                 395                 400

Asp Thr His Ile His Phe Ile Cys Pro Gln Leu Val Asp Glu Ala Leu
                405                 410                 415

Ala Ser Gly Leu Thr Thr Leu Ile Gly Gly Thr Gly Pro Ser Ala
            420                 425                 430

Gly Thr Asn Ala Thr Thr Cys Thr Pro Ser Pro Phe Tyr Met Arg His
            435                 440                 445

Met Leu Ala Ala Thr Asp Gly Leu Pro Met Asn Phe Gly Phe Thr Gly
    450                 455                 460

Lys Gly Asn Asp Ala Gly Pro Thr Ala Ile Glu Glu Ile Val Arg Ala
465                 470                 475                 480

Gly Ala Ser Gly Leu Lys Leu His Glu Asp Trp Gly Thr Thr Pro Ala
                485                 490                 495

Ala Ile Arg Asn Cys Leu Asp Val Ala Asp Lys Tyr Asp Val Gln Val
                500                 505                 510

Thr Ile His Thr Asp Thr Leu Asn Glu Ser Gly Phe Val Glu Ser Thr
            515                 520                 525

Ile Glu Ala Phe Gly Gly Arg Thr Ile His Thr Tyr His Thr Glu Gly
        530                 535                 540

Ala Gly Gly Gly His Ala Pro Asp Ile Ile Val Val Cys Gly Gln Asn
545                 550                 555                 560

Asn Val Leu Pro Ser Ser Thr Asn Pro Thr Arg Pro Tyr Ala Lys Asn
                565                 570                 575

Thr Leu Asp Glu His Leu Asp Met Leu Met Val Cys His His Leu Asp
            580                 585                 590

Lys Ser Ile Pro Glu Asp Leu Asp Phe Ala Glu Ser Arg Ile Arg Ala
        595                 600                 605

Glu Thr Val Ala Ala Glu Asp Val Leu His Asp Ile Gly Ala Ile Ser
610                 615                 620

Met Ile Ser Ser Asp Ser Gln Ala Met Gly Arg Ile Gly Glu Val Ile
625                 630                 635                 640

Ser Arg Thr Trp Arg Thr Ala Ser Lys Met Arg Glu Val Arg Gly Pro
                645                 650                 655

Leu Thr Asp Leu Gly Asp Asp Gly Arg Lys Asp Asn Ala Arg Val Lys
            660                 665                 670

Arg Tyr Ile Ala Lys Tyr Thr Val Asn Pro Ala Ile Ala His Gly Ile
        675                 680                 685

Ser His Leu Val Gly His Val Ala Val Gly Thr Leu Ala Asp Leu Val
    690                 695                 700

Leu Trp Lys Pro Glu Asn Phe Gly Ser Lys Pro Glu Met Ile Leu Lys
705                 710                 715                 720

Ala Gly Val Ile Thr Tyr Ser Gln Met Gly Asp Ala Asn Ala Ser Ile
                725                 730                 735

Pro Ser Val Gln Pro Phe Tyr Ser Lys Pro Met Trp Gly Ala Lys Pro
            740                 745                 750

Gly Ser Ala Ala Leu Asn Ser Val Ala Phe Val Ser Gln Val Ser Ile
            755                 760                 765

Thr Ser Arg Val Ile Glu Ser Tyr Gly Leu Ser Lys Lys Ile Glu Ala
```

```
                    770                 775                 780
Val Arg Gly Cys Arg Asp Ile Gly Lys Asp Met Lys Trp Asn Asp
785                 790                 795                 800

Thr Thr Pro Ala Met Lys Val Asp Pro Glu Ser Tyr Glu Val Arg Ala
                805                 810                 815

Asp Gly Val Leu Met Asp Val Lys Pro Val Glu Arg Val Ala Leu Ala
                820                 825                 830

Thr Pro Tyr Asn Leu Phe
            835

<210> SEQ ID NO 4
<211> LENGTH: 835
<212> TYPE: PRT
<213> ORGANISM: Schizosaccharomyces pombe

<400> SEQUENCE: 4

Met Gln Pro Arg Glu Leu His Lys Leu Thr Leu His Gln Leu Gly Ser
1               5                   10                  15

Leu Ala Gln Lys Arg Leu Cys Arg Gly Val Lys Leu Asn Lys Leu Glu
                20                  25                  30

Ala Thr Ser Leu Ile Ala Ser Gln Ile Gln Glu Tyr Val Arg Asp Gly
            35                  40                  45

Asn His Ser Val Ala Asp Leu Met Ser Leu Gly Lys Asp Met Leu Gly
        50                  55                  60

Lys Arg His Val Gln Pro Asn Val Val His Leu Leu His Glu Ile Met
65              70                  75                  80

Ile Glu Ala Thr Phe Pro Asp Gly Thr Tyr Leu Ile Thr Ile His Asp
                85                  90                  95

Pro Ile Cys Thr Thr Asp Gly Asn Leu Glu His Ala Leu Tyr Gly Ser
            100                 105                 110

Phe Leu Pro Thr Pro Ser Gln Glu Leu Phe Pro Leu Glu Glu Glu Lys
        115                 120                 125

Leu Tyr Ala Pro Glu Asn Ser Pro Gly Phe Val Glu Val Leu Glu Gly
    130                 135                 140

Glu Ile Glu Leu Leu Pro Asn Leu Pro Arg Thr Pro Ile Glu Val Arg
145                 150                 155                 160

Asn Met Gly Asp Arg Pro Ile Gln Val Gly Ser His Tyr His Phe Ile
                165                 170                 175

Glu Thr Asn Glu Lys Leu Cys Phe Asp Arg Ser Lys Ala Tyr Gly Lys
            180                 185                 190

Arg Leu Asp Ile Pro Ser Gly Thr Ala Ile Arg Phe Glu Pro Gly Val
        195                 200                 205

Met Lys Ile Val Asn Leu Ile Pro Ile Gly Ala Lys Leu Ile Gln
    210                 215                 220

Gly Gly Asn Ser Leu Ser Lys Gly Val Phe Asp Asp Ser Arg Thr Arg
225                 230                 235                 240

Glu Ile Val Asp Asn Leu Met Lys Gln Gly Phe Met His Gln Pro Glu
                245                 250                 255

Ser Pro Leu Asn Met Pro Leu Gln Ser Ala Arg Pro Phe Val Val Pro
            260                 265                 270

Arg Lys Leu Tyr Ala Val Met Tyr Gly Pro Thr Thr Asn Asp Lys Ile
        275                 280                 285

Arg Leu Gly Asp Thr Asn Leu Ile Val Arg Val Glu Lys Asp Phe Thr
    290                 295                 300
```

```
Glu Tyr Gly Asn Glu Ser Val Phe Gly Gly Lys Val Ile Arg Asp
305                 310                 315                 320

Gly Thr Gly Gln Ser Ser Lys Ser Met Asp Glu Cys Leu Asp Thr
            325                 330                 335

Val Ile Thr Asn Ala Val Ile Ile Asp His Thr Gly Ile Tyr Lys Ala
                340                 345                 350

Asp Ile Gly Ile Lys Asn Gly Tyr Ile Val Gly Ile Gly Lys Ala Gly
            355                 360                 365

Asn Pro Asp Thr Met Asp Ile Gly Glu Asn Met Val Ile Gly Ser
    370                 375                 380

Ser Thr Asp Val Ile Ser Ala Glu Asn Lys Ile Val Thr Tyr Gly Gly
385                 390                 395                 400

Met Asp Ser His Val His Phe Ile Cys Pro Gln Gln Ile Glu Glu Ala
                405                 410                 415

Leu Ala Ser Gly Ile Thr Thr Met Tyr Gly Gly Thr Gly Pro Ser
            420                 425                 430

Thr Gly Thr Asn Ala Thr Thr Cys Thr Pro Asn Lys Asp Leu Ile Arg
            435                 440                 445

Ser Met Leu Arg Ser Thr Asp Ser Tyr Pro Met Asn Ile Gly Leu Thr
    450                 455                 460

Gly Lys Gly Asn Asp Ser Gly Ser Ser Leu Lys Glu Gln Ile Glu
465                 470                 475                 480

Ala Gly Cys Ser Gly Leu Lys Leu His Glu Asp Trp Gly Ser Thr Pro
                485                 490                 495

Ala Ala Ile Asp Ser Cys Leu Ser Val Cys Asp Glu Tyr Asp Val Gln
                500                 505                 510

Cys Leu Ile His Thr Asp Thr Leu Asn Glu Ser Ser Phe Val Glu Gly
            515                 520                 525

Thr Phe Lys Ala Phe Lys Asn Arg Thr Ile His Thr Tyr His Val Glu
    530                 535                 540

Gly Ala Gly Gly Gly His Ala Pro Asp Ile Ile Ser Leu Val Gln Asn
545                 550                 555                 560

Pro Asn Ile Leu Pro Ser Ser Thr Asn Pro Thr Arg Pro Phe Thr Thr
                565                 570                 575

Asn Thr Leu Asp Glu Glu Leu Asp Met Leu Met Val Cys His His Leu
            580                 585                 590

Ser Arg Asn Val Pro Glu Asp Val Ala Phe Ala Glu Ser Arg Ile Arg
    595                 600                 605

Ala Glu Thr Ile Ala Ala Glu Asp Ile Leu Gln Asp Leu Gly Ala Ile
610                 615                 620

Ser Met Ile Ser Ser Asp Ser Gln Ala Met Gly Arg Cys Gly Glu Val
625                 630                 635                 640

Ile Ser Arg Thr Trp Lys Thr Ala His Lys Asn Lys Leu Gln Arg Gly
            645                 650                 655

Ala Leu Pro Glu Asp Glu Gly Ser Gly Val Asp Asn Phe Arg Val Lys
    660                 665                 670

Arg Tyr Val Ser Lys Tyr Thr Ile Asn Pro Ala Ile Thr His Gly Ile
    675                 680                 685

Ser His Ile Val Gly Ser Val Glu Ile Gly Lys Phe Ala Asp Leu Val
    690                 695                 700

Leu Trp Asp Phe Ala Asp Phe Gly Ala Arg Pro Ser Met Val Leu Lys
705                 710                 715                 720

Gly Gly Met Ile Ala Leu Ala Ser Met Gly Asp Pro Asn Gly Ser Ile
```

```
            725                 730                 735
Pro Thr Val Ser Pro Leu Met Ser Trp Gln Met Phe Gly Ala His Asp
            740                 745                 750

Pro Glu Arg Ser Ile Ala Phe Val Ser Lys Ala Ser Ile Thr Ser Gly
            755                 760                 765

Val Ile Glu Ser Tyr Gly Leu His Lys Arg Val Glu Ala Val Lys Ser
            770                 775                 780

Thr Arg Asn Ile Gly Lys Lys Asp Met Val Tyr Asn Ser Tyr Met Pro
785                 790                 795                 800

Lys Met Thr Val Asp Pro Glu Ala Tyr Thr Val Thr Ala Asp Gly Lys
                    805                 810                 815

Val Met Glu Cys Glu Pro Val Asp Lys Leu Pro Leu Ser Gln Ser Tyr
                    820                 825                 830

Phe Ile Phe
            835

<210> SEQ ID NO 5
<211> LENGTH: 569
<212> TYPE: PRT
<213> ORGANISM: Bacillus pasteurii

<400> SEQUENCE: 5

Met Lys Ile Asn Arg Gln Gln Tyr Ala Glu Ser Tyr Gly Pro Thr Val
1               5                   10                  15

Gly Asp Arg Val Arg Leu Ala Asp Thr Asp Leu Gly Glu Val Glu Lys
            20                  25                  30

Asp Tyr Tyr Tyr Leu Gly Asp Glu Val Asn Phe Gly Gly Gly Lys Val
            35                  40                  45

Leu Arg Glu Gly Met Gly Glu Asn Gly Thr Tyr Thr Arg Thr Glu Asn
50                  55                  60

Val Leu Asp Leu Leu Leu Thr Asn Ala Leu Ile Leu Asp Tyr Thr Gly
65                  70                  75                  80

Ile Tyr Lys Ala Asp Ile Gly Val Lys Asp Gly Tyr Ile Val Gly Ile
                85                  90                  95

Gly Lys Gly Gly Asn Pro Asp Ile Met Asp Gly Val Thr Pro Asn Met
            100                 105                 110

Ile Val Gly Thr Ala Thr Glu Val Ile Ala Glu Gly Lys Ile Val
            115                 120                 125

Thr Ala Gly Gly Ile Asp Thr His Val His Phe Ile Asn Pro Asp Gln
            130                 135                 140

Val Asp Val Ala Leu Ala Asn Gly Ile Thr Thr Leu Phe Gly Gly Gly
145                 150                 155                 160

Thr Gly Pro Ala Glu Gly Ser Lys Ala Thr Thr Val Thr Pro Gly Pro
                165                 170                 175

Trp Asn Ile Glu Lys Met Leu Lys Ser Thr Glu Gly Leu Pro Ile Asn
            180                 185                 190

Val Gly Ile Leu Gly Lys Gly His Gly Ser Ser Ile Ala Pro Ile Met
            195                 200                 205

Glu Gln Ile Asp Ala Gly Ala Ala Gly Leu Lys Ile His Glu Asp Trp
            210                 215                 220

Gly Ala Thr Pro Ala Ser Ile Asp Arg Ser Leu Thr Val Ala Asp Glu
225                 230                 235                 240

Ala Asp Val Gln Val Ala Ile His Ser Asp Thr Leu Asn Glu Ala Gly
                245                 250                 255
```

```
Phe Leu Glu Asp Thr Val Arg Ala Ile Asn Gly Arg Val Ile His Ser
                260                 265                 270

Phe His Val Glu Gly Ala Gly Gly His Ala Pro Asp Ile Met Ala
            275                 280                 285

Met Ala Gly His Pro Asn Val Leu Pro Ser Ser Thr Asn Pro Thr Arg
        290                 295                 300

Pro Phe Thr Val Asn Thr Ile Asp Glu His Leu Asp Met Leu Met Val
305                 310                 315                 320

Cys His His Leu Lys Gln Asn Ile Pro Glu Asp Val Ala Phe Ala Asp
                325                 330                 335

Ser Arg Ile Arg Pro Glu Thr Ile Ala Ala Glu Asp Ile Leu His Asp
            340                 345                 350

Leu Gly Ile Ile Ser Met Met Ser Thr Asp Ala Leu Ala Met Gly Arg
                355                 360                 365

Ala Gly Glu Met Val Leu Arg Thr Trp Gln Thr Ala Asp Lys Met Lys
        370                 375                 380

Lys Gln Arg Gly Pro Leu Ala Glu Glu Lys Asn Gly Ser Asp Asn Phe
385                 390                 395                 400

Arg Leu Lys Arg Tyr Val Ser Lys Tyr Thr Ile Asn Pro Ala Ile Ala
                405                 410                 415

Gln Gly Met Ala His Glu Val Gly Ser Ile Glu Glu Gly Lys Phe Ala
            420                 425                 430

Asp Leu Val Leu Trp Glu Pro Lys Phe Phe Gly Val Lys Ala Asp Arg
        435                 440                 445

Val Ile Lys Gly Gly Ile Ile Ala Tyr Ala Gln Ile Gly Asp Pro Ser
450                 455                 460

Ala Ser Ile Pro Thr Pro Gln Pro Val Met Gly Arg Arg Met Tyr Gly
465                 470                 475                 480

Thr Val Gly Asp Leu Ile His Asp Thr Asn Ile Thr Phe Met Ser Lys
                485                 490                 495

Ser Ser Ile Gln Gln Gly Val Pro Ala Lys Leu Gly Leu Lys Arg Arg
            500                 505                 510

Ile Gly Thr Val Lys Asn Cys Arg Asn Ile Gly Lys Lys Asp Met Lys
        515                 520                 525

Trp Asn Asp Val Thr Thr Asp Ile Asp Ile Asn Pro Glu Thr Tyr Glu
530                 535                 540

Val Lys Val Asp Gly Glu Val Leu Thr Cys Glu Pro Val Lys Glu Leu
545                 550                 555                 560

Pro Met Ala Gln Arg Tyr Phe Leu Phe
                565

<210> SEQ ID NO 6
<211> LENGTH: 566
<212> TYPE: PRT
<213> ORGANISM: Pseudomonas syringae

<400> SEQUENCE: 6

Met Lys Ile Ser Arg Gln Ala Tyr Ala Asp Met Phe Gly Pro Thr Val
1               5                   10                  15

Gly Asp Lys Val Arg Leu Ala Asp Thr Glu Leu Trp Ile Glu Val Glu
            20                  25                  30

Lys Asp Phe Thr Thr Tyr Gly Glu Glu Val Lys Phe Gly Gly Gly Lys
        35                  40                  45

Val Ile Arg Asp Gly Met Gly Gln Gly Gln Leu Leu Ala Ala Glu Val
50                  55                  60
```

-continued

Val Asp Thr Leu Ile Thr Asn Ala Leu Ile Ile Asp His Trp Gly Ile
65                  70                  75                  80

Val Lys Ala Asp Val Gly Ile Lys Asn Gly Arg Ile Ala Ala Ile Gly
                85                  90                  95

Lys Ala Gly Asn Pro Asp Ile Gln Pro Asp Val Thr Ile Ala Val Gly
            100                 105                 110

Ala Ala Thr Glu Val Ile Ala Gly Glu Gly Met Ile Leu Thr Ala Gly
            115                 120                 125

Gly Val Asp Thr His Ile His Phe Ile Cys Pro Gln Gln Ile Glu Glu
130                 135                 140

Ala Leu Met Ser Gly Val Thr Thr Met Ile Gly Gly Gly Thr Gly Pro
145                 150                 155                 160

Ala Thr Gly Thr Asn Ala Thr Thr Val Thr Pro Gly Pro Trp His Met
                165                 170                 175

Ala Arg Met Leu Gln Ala Ser Asp Ser Phe Pro Met Asn Ile Gly Phe
            180                 185                 190

Thr Gly Lys Gly Asn Val Ser Leu Pro Gly Pro Leu Ile Glu Gln Val
        195                 200                 205

Lys Ala Gly Ala Ile Gly Leu Lys Leu His Glu Asp Trp Gly Thr Thr
210                 215                 220

Pro Ala Ala Ile Asp Asn Cys Leu Ser Val Ala Asp Glu Tyr Asp Val
225                 230                 235                 240

Gln Val Ala Ile His Thr Asp Thr Leu Asn Glu Ser Gly Phe Val Glu
                245                 250                 255

Thr Thr Leu Ala Ala Phe Lys Asn Arg Thr Ile His Thr Tyr His Thr
            260                 265                 270

Glu Gly Ala Gly Gly Gly His Ala Pro Asp Ile Ile Lys Ala Cys Gly
        275                 280                 285

Ser Pro Asn Val Leu Pro Ser Ser Thr Asn Pro Thr Arg Pro Phe Thr
290                 295                 300

Arg Asn Thr Ile Asp Glu His Leu Asp Met Leu Met Val Cys His His
305                 310                 315                 320

Leu Asp Pro Ser Ile Ala Glu Asp Val Ala Phe Ala Glu Ser Arg Ile
                325                 330                 335

Arg Arg Glu Thr Ile Ala Ala Glu Asp Ile Leu His Asp Leu Gly Ala
            340                 345                 350

Phe Ser Met Leu Ser Ser Asp Ser Gln Ala Met Gly Arg Val Gly Glu
        355                 360                 365

Val Ile Met Arg Thr Trp Gln Thr Ala Asp Lys Met Lys Lys Gln Arg
370                 375                 380

Gly Pro Leu Pro Gln Asp Gly Pro Gly Asn Asp Asn Phe Arg Ala Lys
385                 390                 395                 400

Arg Tyr Ile Ala Lys Tyr Thr Ile Asn Pro Ala Ile Thr His Gly Ile
                405                 410                 415

Ser His Glu Val Gly Ser Ile Glu Val Gly Lys Trp Ala Asp Leu Val
            420                 425                 430

Leu Trp Arg Pro Ala Phe Phe Gly Val Lys Pro Thr Leu Ile Leu Lys
        435                 440                 445

Gly Gly Ala Ile Ala Ala Ser Leu Met Gly Asp Ala Asn Ala Ser Ile
450                 455                 460

Pro Thr Pro Gln Pro Val His Tyr Arg Pro Met Phe Ala Ser Phe Gly
465                 470                 475                 480

-continued

```
Ser Ser Leu His Ala Thr Ser Leu Thr Phe Ile Ser Gln Ala Ala Phe
            485             490             495

Asp Ala Gly Val Pro Glu Ser Leu Gly Leu Lys Lys Gln Ile Gly Val
            500             505             510

Val Lys Gly Cys Arg Thr Val Gln Lys Lys Asp Leu Ile His Asn Asp
            515             520             525

Tyr Leu Pro Asp Ile Glu Val Asp Pro Gln Thr Tyr Gln Val Lys Ala
    530             535             540

Asp Gly Val Leu Leu Trp Cys Glu Pro Ala Asp Val Leu Pro Met Ala
545             550             555             560

Gln Arg Tyr Phe Leu Phe
            565
```

MINERAL PRECIPITATION METHODS

CROSS-REFERENCE

This application is a U.S. national phase of International Application No. PCT/US2014/062557, filed on Oct. 28, 2014, which claims priority to U.S. Provisional Application No. 61/896,340, filed Oct. 28, 2013, and U.S. Provisional Application No. 61/916,908, filed Dec. 17, 2013, all of which are incorporated by reference herein in their entirety.

STATEMENT OF U.S. GOVERNMENT INTEREST

This invention was made with government support under grant number 1233658 awarded by the National Science Foundation and grant number 0856801 by the National Science Foundation. The government has certain rights in the invention.

SUMMARY OF THE INVENTION

The present invention provides mineral precipitation methods, comprising
combining a porous starting material with
(i) a source of urease;
(ii) urea; and
(iii) a source of divalent cations;
wherein (i), (ii), (and iii) are provided in amounts effective and the combining is carried out under conditions suitable to cause carbonate mineral precipitation of the starting material to produce a starting material complex; and (b) contacting the starting material complex with a base under conditions to mitigate formation of ammonium salts in the starting material complex. In one embodiment, the base is introduced into the starting material complex at one or more locations. In another embodiment, contacting the starting material complex with the base results in an increased pH of the starting material complex at the site of the contacting. In various further embodiments, the base is selected from the group consisting of NaOH, KOH, Ca(OH)$_2$, Mg(OH)$_2$, and combinations thereof. In one embodiment, the source of urease comprises isolated urease or cells expressing urease.

In various non-limiting embodiments, the method can be used for one or more of improving bearing capacity of foundations; reducing settlement potential of foundations or embankments; stabilizing slopes; reducing the potential for triggering earthquake-induced liquefaction; reducing the potential for triggering static liquefaction; mitigating the potential for damaging ground displacements subsequent to triggering of liquefaction; increasing lateral resistance of foundations; enhancing stability of slopes or embankments; lateral earth pressures on retaining walls; increasing passive resistance of retaining walls; increasing capacity of ground anchors or soil nails; increasing the side resistance and tip resistance of deep foundations; facilitating tunneling in running or flowing ground; stabilizing excavation bottoms; soil erosion control; and groundwater control.

In various further embodiments, the starting material can be selected from the group consisting of sand, silt, clay, other sediments, sawdust, igneous rocks, metamorphic rocks, gravel, fractured crystalline rocks, cracked concrete and sedimentary rocks including but not limited to conglomerate, breccia, sandstone, siltstone, shale, limestone, gypsum, and dolostone, and combinations thereof. In other embodiments, the source of divalent cations is selected from the group consisting of calcium, magnesium, strontium, and other cations in the divalent state such as iron, cadmium, manganese, lead, or zinc ions, or combinations thereof. In a further embodiment, the method further comprises introducing a clay slurry into the starting material prior to or concurrent with combining the starting material with the source of urease, the urea, and the source of divalent cations.

DETAILED DESCRIPTION OF THE INVENTION

Figure 1:
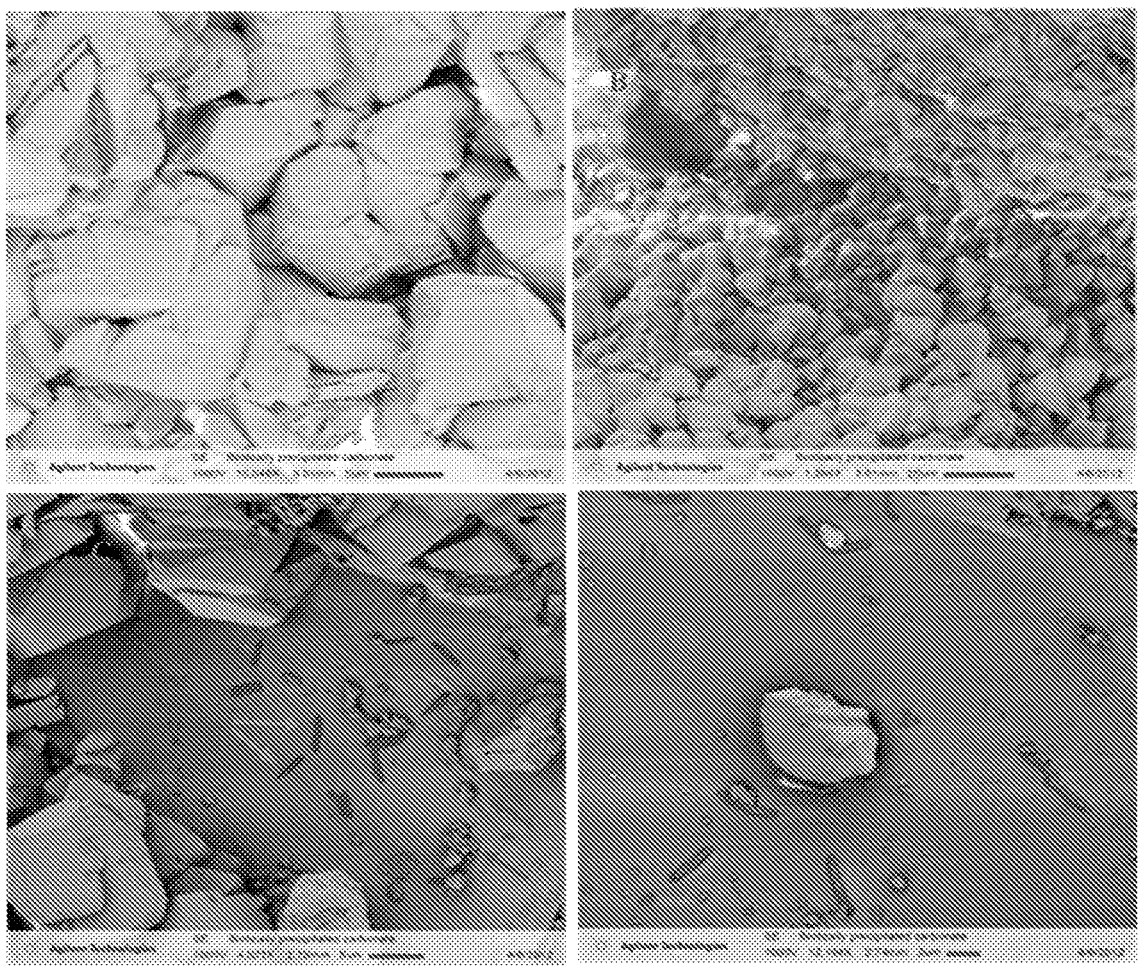
FIG. 1. LV-Scanning electron microscope images of a) well-grown and cementing calcite crystals; b) cementing calcite crystals at inter-particle contact; c) indention of quartz surface (arrows) and nucleation of calcite crystals (red arrows); d) calcite crystal growing on quartz surface.

As used herein, the singular forms "a", n and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

In a first aspect, the present invention provides mineral precipitation method, comprising
  (a) combining a porous starting material with
    (i) a source of urease;
    (ii) urea; and
    (iii) a source of divalent cations;
  wherein (i), (ii), (and (iii) are provided in amounts effective and the combining is carried out under conditions suitable to cause carbonate mineral precipitation within the starting material to produce a starting material complex; and
  (b) contacting the starting material complex with a base under conditions to mitigate formation of ammonium salts in the starting material complex.

In a soil cementation process based upon carbonate precipitation via hydrolysis of urea, adding a base (such as sodium hydroxide) can mitigate the formation of ammonium salts, inhibit nitrification of ammonia (which can lower the pH and start dissolving CaCO$_3$), and facilitate carbonate precipitation and cementation. It is applicable to work on enzyme-induced calcite precipitation (EICP) as described herein, as well as microbially induced calcite precipitation (MICP). The use of the base helps drive a shift of ammonium→ammonia to limit the potential of reaction reversal due to the ammonium, and will temporarily increase pH near the point of introduction, which also has a beneficial effect with respect to inducing carbonate precipitation. This not only limits the potential for reversal of and enhances carbonate precipitation, but also helps rid the system of toxic ammonium salt by-products. A further effect of adding a strong base to the system is that it may help expose/dissolve some of the soil particle or substances clothing the soil particle and thereby facilitate more and/or stronger bonding of the soil to be improved (e.g. gravel, sand, or silt particles susceptible to degradation/dissolution via base) with the precipitated calcite (calcium carbonate).

Induced carbonate precipitation can enhance the stiffness, strength, and liquefaction resistance of soil. The methods provide an alternative to commonly used soil improvement techniques such as deep soil mixing, stone columns, penetration and compaction grouting, and rammed aggregate piers.

The methods can be used, for example, in stabilizing slopes, improving the bearing capacity of foundations, reducing settlement potential of foundations and embankments, increasing the lateral resistance of foundations, reducing the potential for triggering of earthquake-induced liquefaction; reducing the potential for triggering static liquefaction, mitigating the potential for damaging ground displacements subsequent to triggering of liquefaction; enhancing the stability of slopes and embankments, reducing lateral earth pressures on retaining walls, increasing the passive resistance of retaining walls, increasing the capacity of ground anchors and soil nails, increasing the side resistance and tip resistance of deep foundations, facilitating tunneling in running or flowing ground (dry or saturated cohesionless soil), stabilizing the bottom of excavations, soil erosion control, groundwater control.

Any suitable base may be used that serves to mitigate formation of ammonium salts in the starting material complex. In one non-limiting embodiment, the base is selected from the group consisting of NaOH, KOH, Ca(OH)$_2$, Mg(OH)$_2$, and combinations thereof. The amount of base needed is that amount which shifts the acid-base equilibria towards the basic side (i.e., higher pH); this amount will depend on the concentration and the amount of concentrations of urea and divalent cations added to the starting material (or in the starting material complex) used, as will be understood by those of skill in the art. In addition, soil conditions may favor more or less base as certain soils lack buffering capacity and other soils provide some level of buffering, respectively. The goal is to add a sufficient amount of base to shift the acid-base equilibria of the chemical reaction matrix to a high pH (preferably pH>10) which would greatly favor ammonia over ammonium. Thus, as will be understood by those of skill in the art, a lesser amount of stronger base (e.g., higher Molarity or dibasic base) can be used, or a greater amount of a weaker base (e.g., lower Molarity or monbasic). The exact amount of base added will depend on the concentration of ammonium present in the reacting system, or the amount expected to be formed in the reacting system.

In one embodiment, the base is contacted with the starting material complex after most of the carbonate precipitation reaction has occurred, or after nearly all the urea has been hydrolyzed; these are two different reactions, and even if most to all the urea is depleted, carbonate precipitation may still be occurring and can be further "stimulated" or driven by addition of base—again, by shifting the system to more basic conditions which favor mineral precipitation. The timing of contacting can be determined by those of skill in the art based on the intended use. In one non-limiting example, one could draw a sample and test concentrations of either calcium or urea or both and then estimate the extent of the reaction and add base accordingly. In another embodiment the pH can be checked at appropriate intervals and base added as necessary for the intended use. In various further embodiments, the method may comprise checking the pH of the complex at a location of interest to estimate or determine the ammonia-ammonium concentrations, including but not limited to checking Ca, NH$_3$ and/or NH$_4$ levels, which can be used to estimate/determine the ammonia-ammonium ratios, and/or estimate/determine the extent/amount of carbonate precipitation.

The contacting; can be carried out for as long as appropriate for an intended use. As will be understood by those of skill in the art, upon contacting of the complex with the base, the reaction and shift from ammonium to ammonia occurs very rapidly, but may be spatially limited to areas near a site of contacting the complex with the base. Thus, in one embodiment, the methods may comprise introducing the base into the complex at more than one location in the complex. Any suitable number of different locations for contacting of the complex with the base can be used, as deemed most appropriate for an intended use.

The base can be contacted with the complex via any suitable technique, including but not limited to injection or percolation of the base into the starting complex, or via any other means of introducing the base into the complex.

"Carbonate mineral precipitation" means mineral precipitates that may include one or more cations that may produce one of several phases of carbonate minerals, including but not limited to calcite. In a preferred embodiment, calcium carbonate precipitates form cementation bonds at inter-particle contacts in the starting material and fill in void spaces in the starting materials (thereby increasing the tendency of the starting material to dilate, or expand in volume, when sheared), and/or cementation of adjacent particles of the starting material.

Several divalent cations, primarily alkaline earth metals and other divalent-state metals (including but not limited to such as calcium, magnesium, strontium, iron, cadmium, manganese, lead, or zinc ions, or combinations thereof), that satisfy the crystalline structure constraints of calcite or calcium mineral carbonates can be used to precipitate carbonate minerals in the present methods. Any suitable source of divalent cations can be used, including but not limited to salts of organic and inorganic compounds such as nitrates, nitrites, chlorides, sulfates, oxides, acetates, silicates, oxalates or mixtures thereof.

The appropriate amount of ions can be determined by one of skill in the art based on the teachings herein; factors to be considered in determining an appropriate amount of ions include, but are not limited the required amount of carbonate precipitate required for the particular application as determined on a stoichiometric basis. In one non-limiting example, if 100 grams (approximately 1 mole) of calcium carbonate ($CaCO_3$) is desired, then 1 mole of urea ($(NH_2)_2CO$) and at least 1 mole of calcium ($Ca^{2+}$) are required (in addition to alkalinity, the urea also provides the necessary 1 mole of carbon to ultimately form $CO_3^{2-}$).

Any suitable starting material, or combinations of starting materials, may be used in the methods of the invention, such as those having a particulate structure or those consisting of discrete soil particles forming a stable framework (or skeleton) or relatively impervious blocks delineated by an interconnected network of fractures or fissures. In a preferred embodiment, the starting material may be unconsolidated or partially consolidated particulate material such as sand, silt, soil, clay, sediments, sawdust or other material that is amenable to in situ cementation, or combinations thereof. As used herein, "particulate" starting materials are starting materials comprising separate particles.

In another embodiment, the starting material may comprise fractured rock masses. Such starting materials may be mixed in situ or mixed and compacted with the urease, the urea, and the source of divalent cations. In a further embodiment, the starting material is saturated.

In further embodiments, the starting material may be gravel, igneous, metamorphic, or sedimentary rocks including but not limited to conglomerate, breccia, sandstone, siltstone, shale, limestone, gypsum, and dolostone, or combinations thereof. In one preferred embodiment, the starting material comprises sand. In another preferred embodiment, the starting material comprises silt. In a further preferred embodiment, the starting material is fractured crystalline rock or cracked concrete.

The starting material may be "porous" in that it enables sufficient passage of the urease, the urea, and/or the source of calcium or other ions and constituents including, but not limited to, buffers and stabilizers, to enable carbonate precipitation with or without cementation. In some applications, the method may work simply by filling the void spaces (e.g. soil pores, rock fractures) with the carbonate precipitate, without any actual cementation of/bonding to the host material.

The components can be combined in any way suitable in light of the specific starting material, the amount of starting material, the components to be used, etc. In various embodiments, the starting material and components are combined by a technique selected from the group consisting of flushing, injecting, mixing, spraying, dripping or trickling onto or into the starting material. The starting material may also be immersed in one or more ways as described above. In addition, secondary non-specific methods may be employed to facilitate carbonate precipitation including, but not limited to, moisture control measures, crystal seeding, and initiation of nucleation sites. In one embodiment, the methods comprise mixing powdered urease or urease in solution with a particulate starting material prior to percolation of a solution comprising the urea and the divalent ion source or combining the urease, urea, and divalent ion in solution with the starting material, mixing them with in situ or mixing them ex situ and then placing or compacting the mixture. In another embodiment, the combining comprises injection of the urease, urea, and/or divalent cations into the starting material via one or more central porous injection tubes, such as are described in the examples that follow. Any number of such injection tubes may be used, depending on the size and depth of the starting material to be treated, among other factors, and any design or size of such injection tubes may be used. In one non-limiting embodiment, field injection tubes may comprise 2 inch or 3 inch diameter perforated pipe that is vibrated or pushed into the soil. The tubes may be placed at varying depths and orientations in the starting material. In one embodiment, injection occurs all along the length of the tube at once, or may comprise injection over small intervals (such as 1-3 foot intervals) working from one end of the tube, which can be accomplished, for example, by sealing off sections where injection is to occur with packers, as in known in grouting technology.

The source of urease may comprise isolated urease or cells expressing urease.

As used herein, "isolated urease" is urease that is extracted from cells and cellular materials. The urease may be synthetically produced or obtained by extraction from any suitable source, including but not limited to bacteria, plants, invertebrates, and fungi. In one non-limiting embodiment, a plant derived urease extract can be used. For example, urease activity is present in various plant leaves and this activity can be realized using crude extracts of the leaves, or isolated enzyme. Urease enzyme as discussed herein is characterized by the reaction it catalyzes and identified by EC 3.5.1.5 (i.e. Reaction: urea+$H_2O$=$CO_2$+2 $NH_3$). In one embodiment, the urease enzyme is isolated from the jack-bean plant (SEQ ID NO:1). The amino acid sequences of exemplary ureases for use with the present invention are provided below. However, it will be clear to those of skill in the art that any enzyme identified by EC 3.5.1.5 can be used in the methods of the invention, including but not limited to a urease comprising or consisting of any one of SEQ ID NOS: 2-5, where SEQ ID NO:2 is a soybean urease, SEQ ID NO:3 is a *Agaricus bisporus* urease, SEQ ID NO:4 is a *Schizosaccharomyces pompe* (strain 972/ATCC 24843) urease, SEQ ID NO:5 is a *Sporosarcina pasteurii* urease, and SEQ ID NO:6 is a *Pseudomonas syringae* (strain R728a, urease.

The appropriate amount of urease needed can be determined by one of skill in the art based on the teachings herein; factors to be considered in determining an appropriate amount of urease include, but are not limited to:

(a) urease source type (e.g. Jack bean vs. other source, such as a cell expressing urease)

(b) urease purity, which dictates enzymatic activity (i.e. rate of conversion of urea to products); and (c) the stability/half-life of the enzyme matrix used, where the "enzyme matrix" refers to the specific form of the enzyme mixture used such as liquid, powder and/or solid when combined with or used apart from stabilizers, buffers, fillers or other media to facilitate its desired use.

For example, assuming that for practical purposes that transport via diffusion, advection and dispersion is not limiting the availability of urea or calcium to the enzymes—or vice versa—(e.g. we thoroughly mix the soil and cementation constituents or we actively pump the cementation constituents into the soil or do something to assure that the right constituents get to where they need to be), then in a homogenous soil (i.e. without zones of blocked flow or disproportionately high/preferential flow) we could expect an approximately linear relationship between urea conversion and required amount(s) of enzyme needed to convert "x" grams of urea to "y" grams of calcium carbonate over a given time frame. This is also dependent on the on the amount of calcium ions available for precipitation. A sufficiently high concentration of calcium to form calcium carbonate is needed, with hydrolysis of urea just one part of the overall process. If a soil mass requires a total amount "x" grams of urea to be converted into products for calcium carbonate formation, and "y" grams of enzyme can only convert 50% of "x" during its functional life time, then theoretically twice as much enzyme is needed to fully convert "x" grams of urea.

Urea is an organic compound of the chemical formula $CO(NH_2)_2$. Urea is a colorless, odorless, highly water soluble substance with very low toxicity (LD50=12 g/kg for mouse, Agrium MSDS), and is widely commercially available. Any suitable source of urea can be used, including but not limited to those disclosed herein.

The appropriate amount of urea can be determined by one of skill in the art based on the teachings herein: factors to be considered in determining an appropriate amount of urea include, but are not limited, to the amount of carbonate required for the particular application and the desired increase in pH and alkalinity as determined on a stoichiometric basis. As will be understood by those of skill in the art, the amount of carbonate precipitation required varies from one use to another.

It will be understood by those of skill in the art that the step of "combining" the starting material with effective amounts of urease, urea, and cations covers any process that results in the bringing together of the three constituents in a manner that results in precipitation of carbonate minerals in the starting material. The reactants may be added to the starting material simultaneously or sequentially. For example, there may be applications where one or two of the constituents are already present in the starting material, in which case the step of "combining" will involve the addition of only the missing components. In one embodiment, the urea and cations are admixed and then added to the urease prior to application to the starting material. However, it will be appreciated by those of skill in the art that the constituents may be combined in other ways to carry out the method of the invention.

By manipulating the relative effective amounts of the various components, the methods of the present invention enable the user to control carbonate precipitation by controlling the amount of carbonate formed and the rate at which it is formed. This flexibility means the methods of the present invention can be used in a wide range of applications from those that require a reasonably modest increase in the strength, stiffness, or dilatancy or modest decrease in the permeability in the starting material to those that require larger changes in the relevant property. As used herein, "dilatancy" refers to the tendency of a soil to expand in volume during shear. This is an important property, for example, with respect to reducing liquefaction potential.

The effective amounts of the various reactants combined according to the method of the present invention may vary depending, at least, on the amount of urease used, the characteristics of the starting material and the conditions under which precipitation is to occur, the desired final strength, stiffness, dilatancy, or permeability of the treated porous material and the amounts of the other reactants in the reaction mix. The present application enables those of skill in the art to determine the relative amounts of the various reactants required for a given application and to apply the method to various starting materials and for a variety of end uses. The method of the present invention may be adapted to allow for the rate of mineral precipitation to be controlled, as required. When rapid or slow formation of the precipitate is desired the amounts and/or relative amounts of the reagents can be selected accordingly to bring about the desired rate of formation. In one non-limiting example, enhancement of the methods may comprise providing stronger nucleation sites on particles of the starting material by high-pH pretreatment of the particles of the starting material to be improved.

Depending on the requirements of a particular application or mode of use of the present invention, rapid formation of the precipitate may be required. Alternatively it may be preferred for the precipitate to be formed slowly. Based on the teachings herein, those of skill in the art will be able to modify the protocol to attain faster or slower formation of the precipitate.

The methods of the invention may be repeated (once, twice, three times, or more) in order to attain the desired amount of mineral precipitate strength, stiffness increase, or permeability reduction. When the method is repeated to gain incremental increases in strength or stiffness or reduction in permeability, not all of the reagents need to be added each time. For example, residual urease activity may still be sufficient for one or more subsequent rounds of the method. A skilled person is readily able to determine the particular amounts of reagents required for use in subsequent rounds of the method of the present invention.

The methods may be applied in situ without disturbing the starting material. This is particularly important for applications where the starting material is delicate or fragile or for other reasons must not be disturbed. Examples include, but are not limited to, when applied in the field where the starting material to be improved (e.g. made resistant to earthquake-induced liquefaction) is underneath or adjacent to an existing structure or facility that is sensitive to ground movement (e.g. settlement or heave).

As will be understood by those of skill in the art, the methods may comprise use of other components as appropriate for a given use. In one embodiment, the methods may further comprise use of a stabilizer (including but not limited to powdered milk) to increase enzyme stability and functional time. The methods can be carried out under any temperature conditions suitable to promote carbonate cementation.

In another embodiment, the method further comprises introducing a clay slurry into the starting material prior to or concurrent with combining the starting material with the urease, the urea, and the source of divalent cations. This embodiment is particularly useful when the starting material comprises a high permeability starting material (e.g. a coarse-grained soil), as it will help to retain the active components in the starting material where cementation is desired; the clay particles may also serve as nucleation points for carbonate precipitation. As used herein, a "clay slurry" is any clay in suspension. In various non-limiting embodiments, the clay may comprise montmorillonite clay (also known as bentonite), attapulgite, or combinations thereof. The amount of clay slurry, the specific amount of clay in the slurry, and the timing/number of times the clay slurry is administered may vary depending, at least, on the characteristics of the starting material and the conditions under which precipitation is to occur, the desired final strength, stiffness, dilatancy, or permeability of the treated porous material and the amounts of the other reactants in the reaction mix. The present application provides examples that enable those of skill in the art to determine the relative amounts of the clay slurry appropriate for a given application and to apply the method to various starting materials and for a variety of end uses.

In a preferred embodiment, the starting material comprises a column of starting material. As used herein, a "column" refers to relatively linear prisms of soil that are to be stiffened and/or strengthened to reinforce the in situ soil mass and/or transfer load to greater depths in the soil stratum. As will be understood by those of skill in the art, the prism of soil extends below a surface of the starting material, in various embodiments, the column is at least 0.6 meters long and 0.15 meters in diameter. In various further embodiments, the column is at least 1, 2, 3, 4, 5, 6, 7, 8, 9, 10, 15, 20, 25, 50, or more meters long/deep. In various further embodiments, the column is at least 0.2, 0.3, 0.4, 0.5, 0.6, 0.7, 0.8, 0.9, 1, 1.5, 2, or more meters in diameter. In one exemplary embodiment, for the mitigation of earthquake-induced liquefaction under residential structures, the columns are between about 0.3 meters to 1.5 meters in diameter; more preferably about 0.9 meters in diameter and up to 20 meters long, in this embodiment, the methods comprise combining the starting materials so that carbonate precipitation of the starting material occur at in a radial pattern around an injection tube (e.g. perforated pipe) to form the column. In one embodiment, carbonate precipitation occurs at only one or more specific areas within the column, such as at a specific location where the starting materials are combined within the column (for example, where liquefiable soil strata is intersected by the injection tube). In another embodiment, carbonate precipitation occurs throughout the column.

This embodiment provides further improvements over prior methods, which are focused on improvement of the entire mass of soil in the improvement zone. In this embodiment, the methods permit production of stone-like materials via local cementation. Columns of improved starting materials, such as soils, have broad application in geotechnical practice, including reducing the potential for earthquake-induced liquefaction; mitigating the potential for damaging ground displacements subsequent to earthquake-induced liquefaction, improvement of foundation bearing capacity, support of embankments, slope stabilization, stabilization of the base of excavations, support of underground openings, and a variety of other geotechnical purposes. The limitations associated with bio-plugging can also be mitigated by using this technique to improve columns of soil (rather than the entire soil mass). Such columns of improved starting material possess, for example, increased strength, stiffness, and liquefaction resistance relative to the non-treated starting material. Bio-plugging refers to hindering the mobility of the compounds that were added to the starting material for the purpose of inducing mineral precipitation due the decrease in permeability associated with mineral precipitation, in another embodiment, the methods can be used for fugitive dust control (e.g., wind-blown erosion).

In one non-limiting example, consider a 4.2-meter long, 1-meter diameter column of soil with a porosity of 0.31 is to be improved by precipitating 5% calcium carbonate by weight. This column has a total volume of 3.29 m$^3$ and a pore space of 1.0 m$^3$. Assuming a calcium carbonate density of 2.71 g/cm$^3$(2710 kg/m), approximately 136 kg of CaCO$_3$ is used to precipitate in the improvement zone (i.e. the column). To obtain 136 kg of CaCO$_3$ (1,360 moles), 81.6 kg of urea (1,360 moles) and 54.4 kg of calcium (1,360 moles) are used, assuming that all added constituents are available and used in the reaction process to precipitate CaCO$_3$. Since there are 2 amine groups per urea molecule, 2,720 moles of ammonia nitrogen and 1,360 moles of carbon dioxide are released from 81.6 kg of urea. Assuming a minimum urease activity of 15,000 units/grain urease powder (type 3 urease from Jack bean [Sigma Aldrich]), where one-unit is the release of 1.0 mg ammonia nitrogen from urea in 5 minutes at pH 7.0 at 20° C., then 10 grams of this particular grade of enzyme (150,000 units) will release 150 grams of ammonia nitrogen (8.8 moles) in 5 minutes. Therefore, 26 hours (1546 minutes) are required to fully catalyze the release of carbon dioxide and ammonia from 81.6 kg of urea.

Any suitable technique/configuration for introducing the components into the column may be used as deemed appropriate. For introduction of the urease into columns, injection could be done at one site per column or at multiple sites along the column. If multiple sites, then the concentration may the same or different at the different locations.

In another embodiment, the starting material is saturated. As used herein, "saturated" means that the soil has reached its maximum water content; if any more water is added it will either drain downward, flow upwards, or turn the soil into a suspension wherein there is little to no inter-particle contact. In one example, the saturated starting material is below the water table. When the starting material is below the water table it is usually saturated, unless there is gas in the soil. Saturated zones may also exist above the water table due to capillary rise, with the extent of the saturated zone above the water table depending upon the pore size of the starting material.

In a second aspect, the present invention provides kits comprising
(a) isolated urease;
(b) urea;
(c) a source of divalent cations, preferably calcium ions; and
(d) a base;
wherein (a), (b), (c) and (d) are provided in amounts effective to cause carbonate cementation when combined with a particulate starting material or a starting material complex. In another embodiment, the kit further comprises a clay slurry.

All definitions, embodiments, and combinations thereof of the first aspect apply equally to this second embodiment, unless the context clearly dictates otherwise. Thus, the kits may further contain any of the components or combinations thereof disclosed for use with the methods of the invention, including but not limited to stabilizers, buffers, nucleation aids, etc.

EXAMPLE 1

Carbonate Cementation Via Plant Derived Urease

Methods
Ottawa 20-30 Sand

Laboratory column tests were conducted using plant derived urease to induce calcium carbonate ($CaCO_3$) precipitation in Ottawa 20-30 sand These tests were carried out in 6"×2" (152 mm×51 mm) acrylic tubes and membrane-lined 2.8"×6" (71 mm×152 mm) split molds (for creating specimens for triaxial testing). Three acrylic tubes and two columns for triaxial testing were filled with 20-30 Ottawa silica sand (mean grain size 0.6 mm, coefficient of uniformity 1.1) and treated as follows: tube #1: the sand was dry pluviated via funnel at ≈3" (76 mm) drop height and then received 5 applications of a cementation solution containing urea and calcium chloride mixed with 1.4 g/L enzyme (total solution volume ≈300 ml); tube #2: sand was added in same manner as tube #1 and then received 2 applications (≈150 ml total) of the same cementation solution mixed with 1.4 g/L enzyme; tube #3: the lower-third of tube was filled with sand and dry enzyme (≈3 g), the remainder of the tube contained dry pluviated sand without enzyme, and the tube then received 2 applications (≈150 ml) of the cementation fluid with no enzyme added.

Approximately 100 mL of a pH=7.8 solution containing 383 mM urea (reagent grade, Sigma-Aldrich), 272 mM $CaCl_2$-$2H_2O$ (laboratory grade, Alfa Aesar) was used for the first application in each acrylic tube. Subsequent applications employed approximately 50 mL of a pH=7.6 solution containing 416 mM urea and 289 mM $CaCl_2$-$2H_2O$. Solution concentrations, while variable, were formulated within a reasonably similar range as a matter of convenience. In each application, the cementation fluid was poured into the top of the acrylic tube with the bottom closed off. The cementation fluid was allowed to stand, loosely covered, in the acrylic tube for at least 24 hours and then drained out the bottom of the cylinder. The next application followed immediately after drainage was complete. Drainage was accomplished by puncturing the base of the cylinder with a 20-gauge needle. When drainage was complete, the needle was removed and the puncture was plugged with a dab of silicone. Occasionally, the needle became plugged and an additional needle was inserted through the base. The triaxial columns were filled with sand in the same manner as tube 1 and then received 2 applications (each application ≈250 ml) of cementation solution with 1.4 g/L enzyme.

In each application of cementation fluid, the fluid was added until it rose to approximately ½-inch (12-mm) above the soil line. After 2 applications, tubes #2 and #3 were allowed to air dry for several days and then analyzed. Experimentation with tube #1 was continued for several more days as three more batches of cementation fluid were applied. The last 2 applications of cementation fluid were allowed to slowly drain through the needle in the base immediately after application rather than sit for 24 hours (drainage rate ≈10-25 ml/hour). The triaxial columns were allowed to stand for at least a week after the second cementation fluid application and then drained.

After drainage was complete, the triaxial columns were moved to a triaxial testing device. After draining the specimens from the acrylic tubes and after the completion of the triaxial tests, all samples were triple washed with de-ionized water. Tubes #2 and #3 were separated in 3 layers, while tube #1 was separated into six layers (for better resolution). Each layer from the specimens in the acrylic tubes and the entire mass of the triaxial specimens were acid washed to determine $CaCO_3$ content by oven drying for 48 hours, weighing, digesting with warm 1M HCl, washing, drying, and reweighing to determine carbonate mineral content.

Several of the cemented specimens were analyzed for mineral identification using X-Ray Diffraction (XRD). Samples were ground in an agate mortar and pestle and powdered onto a standard glass slide for analysis. Scanning electron microscopy (SEM) imaging was performed on intact cemented chunks of material with an Agilent 8500 Low-Voltage SEM (LV-SEM). A LV-SEM is a field emission scanning electron microscope capable of imaging insulating materials, such as organic and biological substances without the need for a metal coating and without causing radiation damage to samples.

Ottawa F-60 Sand

A triaxial column was prepared using Ottawa F-60 silica sand (mean grain size 0.275 mm, coefficient of uniformity 1.74) to investigate enzymatic ureolytic $CaCO_3$ precipitation in a finer grained material than Ottawa 20-30 sand. The specimen was prepared in the same manner as described for the triaxial columns for the Ottawa 20-30 sand. The cementation fluid for the first of the two applications contained approximately 2.0 g/L enzyme, 400 mM urea (reagent grade, Sigma-Aldrich), 300 mM $CaCl_2$-$2H_2O$ (laboratory grade, BDH) at pH=7.7. The fluid for the second application contained 1 M urea-$CaCl_2$-$2H_2O$ solution at pH=7.8 without any enzyme. After the test, the triaxial specimen was washed and subject to acid digestion in the same manner as the Ottawa 20-30 triaxial specimens.

Results
Acrylic Tubes

Approximately 100 ml of cementation solution was delivered per application for the first application in each acrylic tube. However, the amount of solution the tube would accept was notably reduced in subsequent applications, when less than 75 ml was typically required to fill the tubes to ≈½ inch (12 mm) above soil line. At the conclusion of the experiment, precipitation was visible along the entire length of tubes 1 and 2. Internally the cementation was variable, with some highly cemented zones and other zones with little to no cementation, Tube 1 yielded mostly small, loose chunks of sand with strong effervescence upon digestion. Most of this column appeared un-cemented and exhibited unusually viscous behavior when wet. A fairly large (compared to column diameter) piece of strongly cemented sand (no(breakable without tools) formed in the deepest layer of tube 1. Tube 2 had many small chunks of weakly cemented sand with strong effervescence upon digestion. Tube 3 had little to no precipitation in the top layer (i.e. this layer did not show any indication of carbonate upon acid digestion.) The deepest layer of tube 3 contained many pieces of weakly cemented sand that effervesced strongly upon digestion. The middle layer of tube 3 contained a few pieces of cemented sand that effervesced moderately upon digestion. The results from the acid washing are presented in Table 1.

TABLE 1

Results from Experiment Set 1 using 20-30 Ottawa silica sand
Summary of Results

| Tube # | Layer | Weight Change via Digestion | Amt. of CaCO$_3$ (g) | Total Amt. CaCO$_3$ (g) | Theor. Max CaCO$_3$ (g) |
|---|---|---|---|---|---|
| 1 | 1 | 11% | 3.57 | 11.8 | ≈14.5 |
|   | 2 | 3.8% | 1.67 |   |   |
|   | 3 | 2.7% | 1.73 |   |   |
|   | 4 | 2.1% | 1.40 |   |   |
|   | 5 | 2.3% | 1.74 |   |   |
|   | 6 | 2.0% | 1.64 |   |   |
| 2 | 1 | 0.76% | 0.63 | 2.07 | ≈4.35 |
|   | 2 | 0.65% | 0.69 |   |   |
|   | 3 | 0.49% | 0.75 |   |   |
| 3 | 1 | 0.23% | 0.31 | 3.57 | ≈4.35 |
|   | 2 | 0.58% | 0.63 |   |   |
|   | 3 | 1.7% | 2.63 |   |   |

The theoretical maximum CaCO$_3$ content s the stoichiometric maximum balanced on initial concentrations. The primary experimental differences between the tests are (1) the number of applications of cementation fluid and (2) the manner in which the urease was delivered. The results indicate that there is greater carbonate precipitation with increasing number of applications, as expected. The data show more precipitation in (or on) the top layer of tubes 1 and 2 but not in tube 3, as the enzyme was physically confined to the lower-third layer in tube 3 during sample preparation. In the top layer of tube 3, where no urease was mixed with the sand, carbonate precipitation was nearly undetectable. There was no visual evidence of precipitation and practically no measurable change in weight of this layer after acidification (weight change=0.23%). In the bottom layer of tube 3, where 3 g of dry enzyme was mixed with the soil, there was a weight change of 1.7% following acid washing. The middle layer of this specimen had a Minor change in weight (0.58%), possibly due to uneven distribution of the layers during preparation or splitting of the specimen or to upward migration of urease from the bottom layer. XRD analysis confirms that calcite is the mineral phase present in the cemented soil chunks. LV-SEM images, presented in FIG. 1, show silica (quartz) sand particles cemented with calcium carbonate and various morphological features associated with the cementation process on the silica surface.

Triaxial Columns

Figure 2:
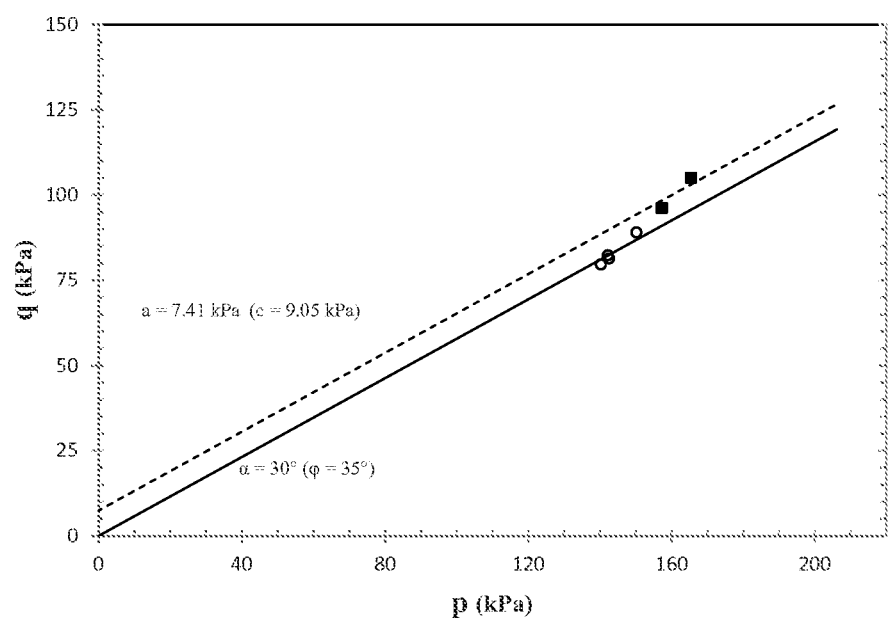
FIG. 2. P-q plot failure envelopes for 20-30 silica sand: ■Cemented ($D_r$=60%); ○ Uncemented ($D_r$=60%).
Figure 3:
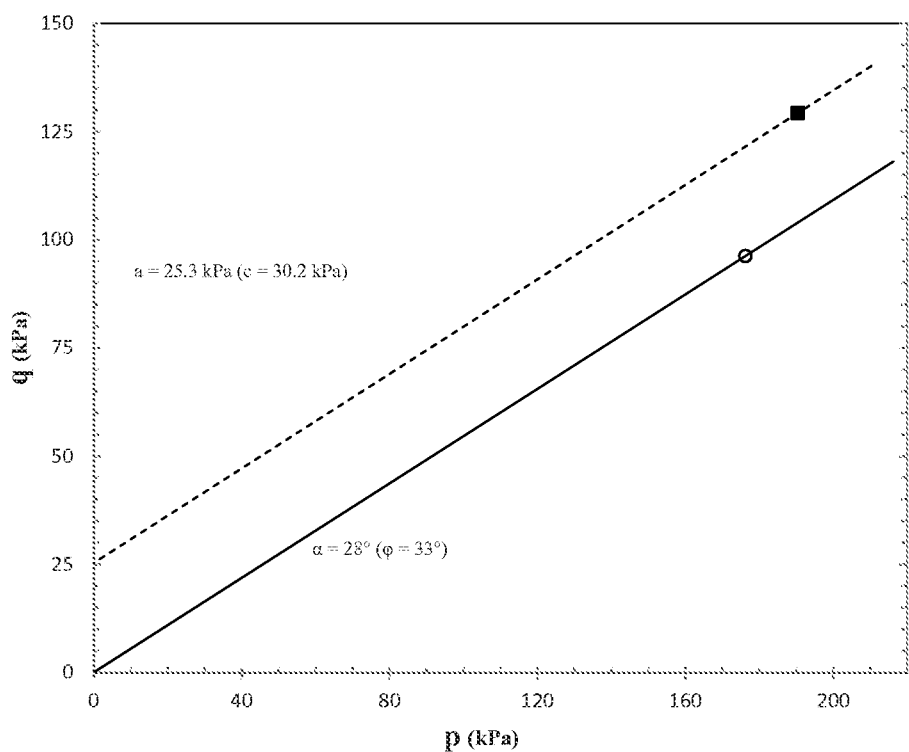
FIG. 3. P-q plot failure envelopes for F-60 silica sand: ■Cemented ($D_r$=35%); ○ Uncemented ($D_r$=37%).

The three triaxial sand columns (2 Ottawa 20-30 sand columns and 1 Ottawa F-60 sand column) were tested in drained triaxial compression prior to acid digestion. All three columns were able to stand upright after removal of the split mold. The results of the triaxial compression tests performed on the 20-30 Ottawa sand are presented in FIG. 2 and the results for the F-60 Ottawa sand are presented in FIG. 4. The carbonate cement content for one of the 20-30 silica sand columns was 2.0% CaCO$_3$ (by weight). The carbonate content of the other 20-30 Ottawa sand column could not be quantified due to unintended sample loss. The carbonate cement content for the finer grained F-60 Ottawa sand was 1.6% CaCO$_3$ (by weight). The results show substantial strength increase for all 3 sand columns tested.

Conclusion

Sand column tests have shown that agriculturally-derived urease can be used to induce calcium carbonate precipitation in sand. Sand columns were developed using Ottawa 20-30 and F-60 sand and three different preparation methods: dry pluviation followed by percolation of a calcium-urease-urea cementation solution, pluviation into a calcium-urease-urea cementation solution, and mixing the sand with urease prior to pluviation with a calcium-urea solution. Cementation was observed in all of the columns. XRD and SEM testing confirmed that calcium carbonate (specifically calcite) was the cementing agent. Acid digestion showed that increased applications yielded correspondingly greater carbonate precipitation. The quality of cementation, as determined by the effort needed to break apart cemented chunks of sand, varied depending on the sampling location within the column. Triaxial test results on cemented columns showed substantial strength increase over non-cemented columns at the same relative density.

EXAMPLE 2

Methods

Three sand columns were constructed in 12" long by 4" (I.D.) clear PVC tubes (schedule 40) and labeled "Column #1," "Column #2," and "Column #3." Column #1 and Column #2 used Ottawa 20-30 sand, a medium (grain size) sand, while Column 3 used Ottawa F60 sand, a fine sand. Each PVC column was closed-off on one end using a flexible cap (Qwik Cap) and fastened with a hose clamp. The 3 columns were filled with densified sand to depth of approximately 4". Next, an injection tube was made of flexible ¼" (O.D.) Tygon tubing with 6-8 needle size holes (18 gauge) in a radial pattern along the last 1.5" of the tubing. The injection tube was then placed along the axis of the column with the end containing needle holes approximately 0.25" above the 4" densified soil layer. The columns were then loosely filled with the designated sand using a small scoop to a height of 10" (i.e., 6" above the 4" base layer). Each column was then filled through the injection tube with approximately 700 mL of tap water at 35° C. in order to fully hydrate the columns—the final water level was just above the top of the soil (i.e. slightly more than 10" from the bottom of the tube). In order to create a uniform soil column, the columns were than densified by firmly tapping the outside of the PVC tube in a radial pattern using a blunt instrument, which reduced the final soil column height from 10" to approximately 9.4" in each column Approximately 40 mL of bentonite slurry was injected into Column #2 through the Tygon injection tube. Each column then received 155 mL of the reaction medium consisting of tap water with 1.36 M urea and 0.765 M calcium chloride dehydrate (pH=7.3, 35° C.). After receiving the reaction medium, the injection tubes were flushed with 2 mL water. Then 15-20 mL of enzyme solution consisting of 0.44 g/L urease enzyme (Sigma Aldrich Type-III, Jack Bean Urease, 26, 100 U/g activity) and 4 g/L stabilizer (nonfat powdered milk) were introduced to each column through the injection tube. Finally, another 3-4 ml, of reaction medium was injected into each column followed by a 2 mL water flush. The injection tubes were closed with polypropylene pinch clamps and the columns were capped with plastic clear wrap and placed in dark, warm (30° C.) environment for 2.8 days. On day 7, an additional 115 mL of reaction medium and 10 mL of enzyme solution was delivered to each column in a manner similar to described above. Approximately 3 ml (0.1% v/v) of 1M NaOH was injected into each column 48 hours before the experiment terminated.

Figure 4:
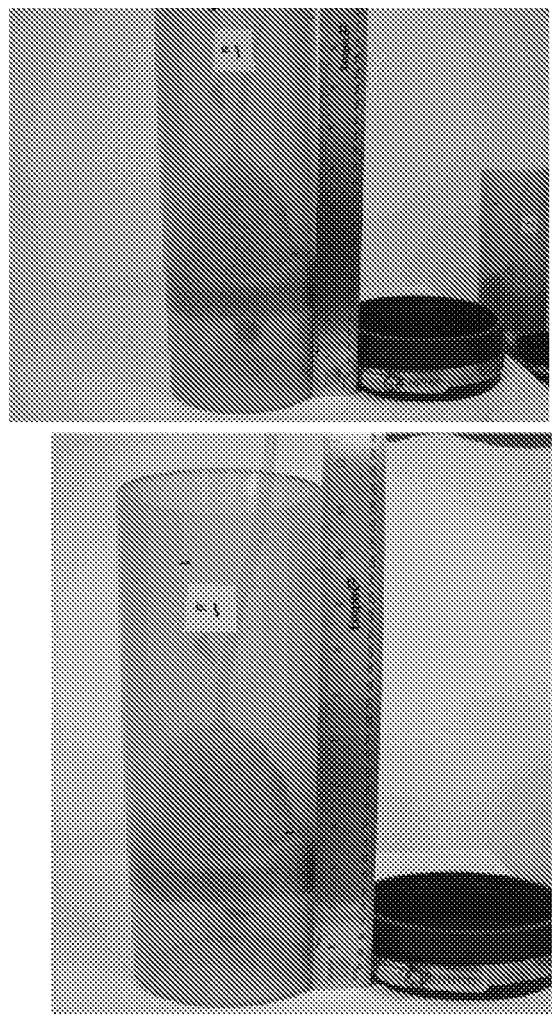
FIG. 4. Results of triaxial compression tests performed using F-60 Ottawa sand (medium sand).

Results:

Upon disassembly, all 3 columns showed strong carbonate cementation in a cylindrical zone around the end of the inject tube. The results varied slightly for each column, as follows:

Column #1 (20-30 medium sand)—A region of strongly cemented soil began ≈2.5" from the column bottom. The cemented zone was ≈4.5" in length and displayed a prominent rounding at the top and a flat surface at the bottom. Overall, the cemented region appeared to have a cylindrical bottom and bulb-shaped upper portion (FIG. 4). Several chunks of cemented soil were dislodged to access the most strongly cemented region which had the injection tube firmly embedded. The cemented region could not be dislodged from the PVC column without the use of hand tools.

Figure 5:
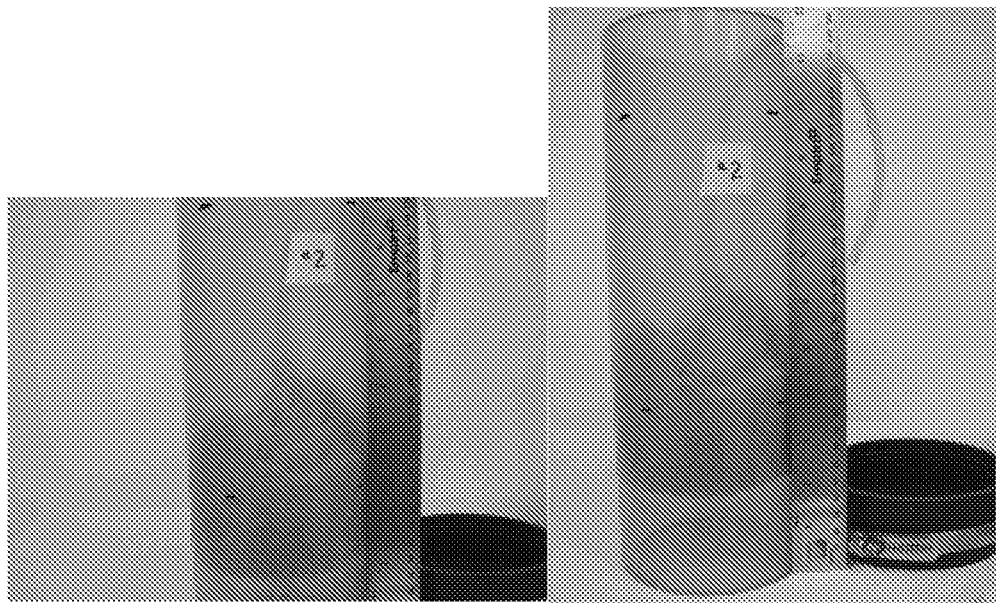
FIG. 5. Results of triaxial compression tests performed using medium sand w/bentonite slurry.

Column #2 (20-30 medium sand w/40 mL bentonite slurry)—A cylindrical region of strongly cemented soil began ≈3" from the column bottom, was ≈4" in length and displayed small rounding near the top and a flat surface at the bottom. Overall, the cemented region was mostly cylindrical (FIG. 5). Several chunks of cemented soil were dislodged to access the most strongly cemented region which had the injection tube loosely embedded. The cemented region could not be dislodged from the PVC column without the use of hand tools.

Figure 6:
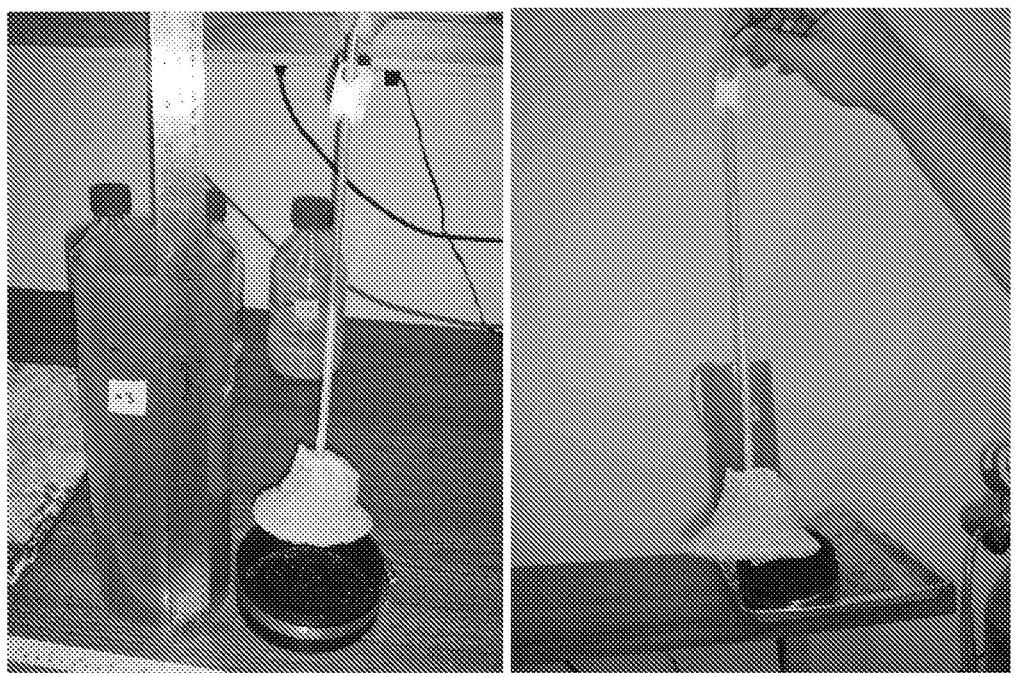
FIG. 6. Results of triaxial compression tests performed using F-60 fine sand.
Figure 7:
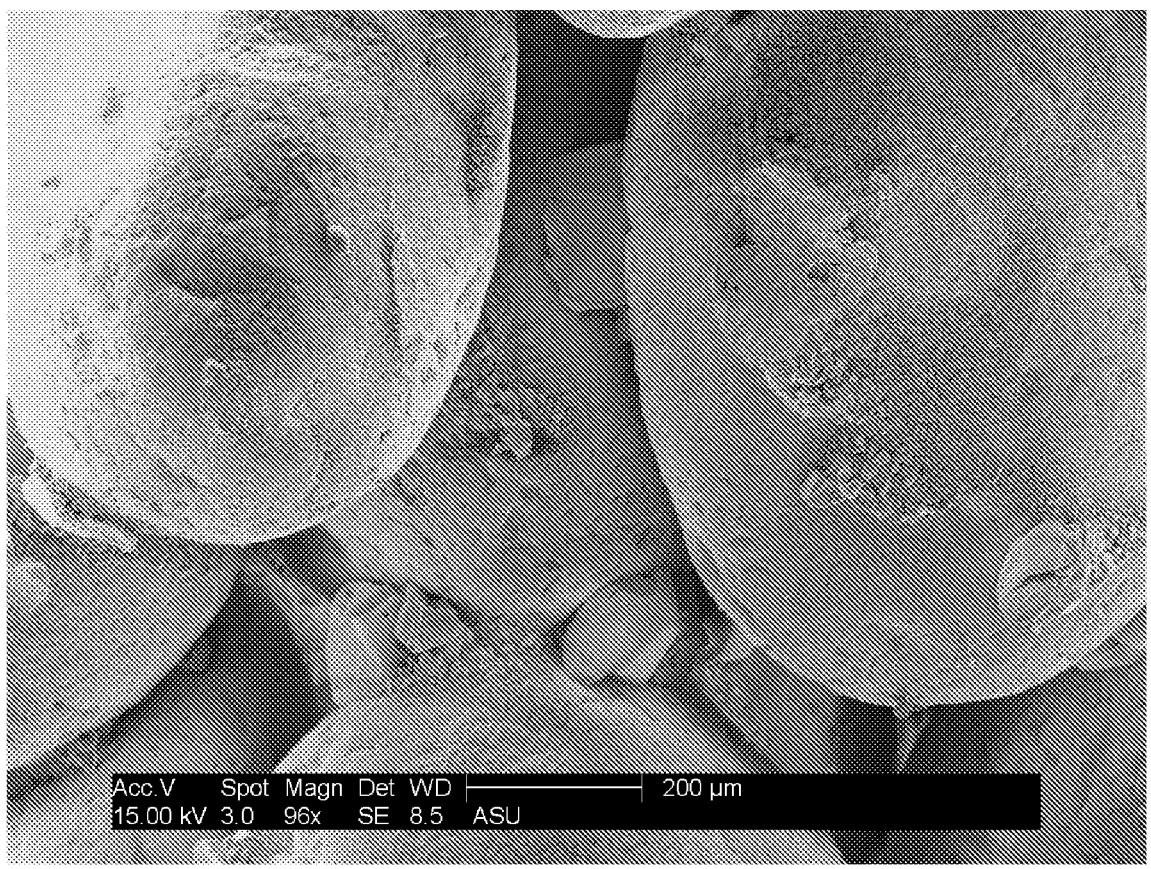
FIG. 7. Image from mix & compact columns using silica 20-30. These are silica sand particles variously covered with CaCO$_3$ and cemented at the inter-particle contacts.
Figure 8:
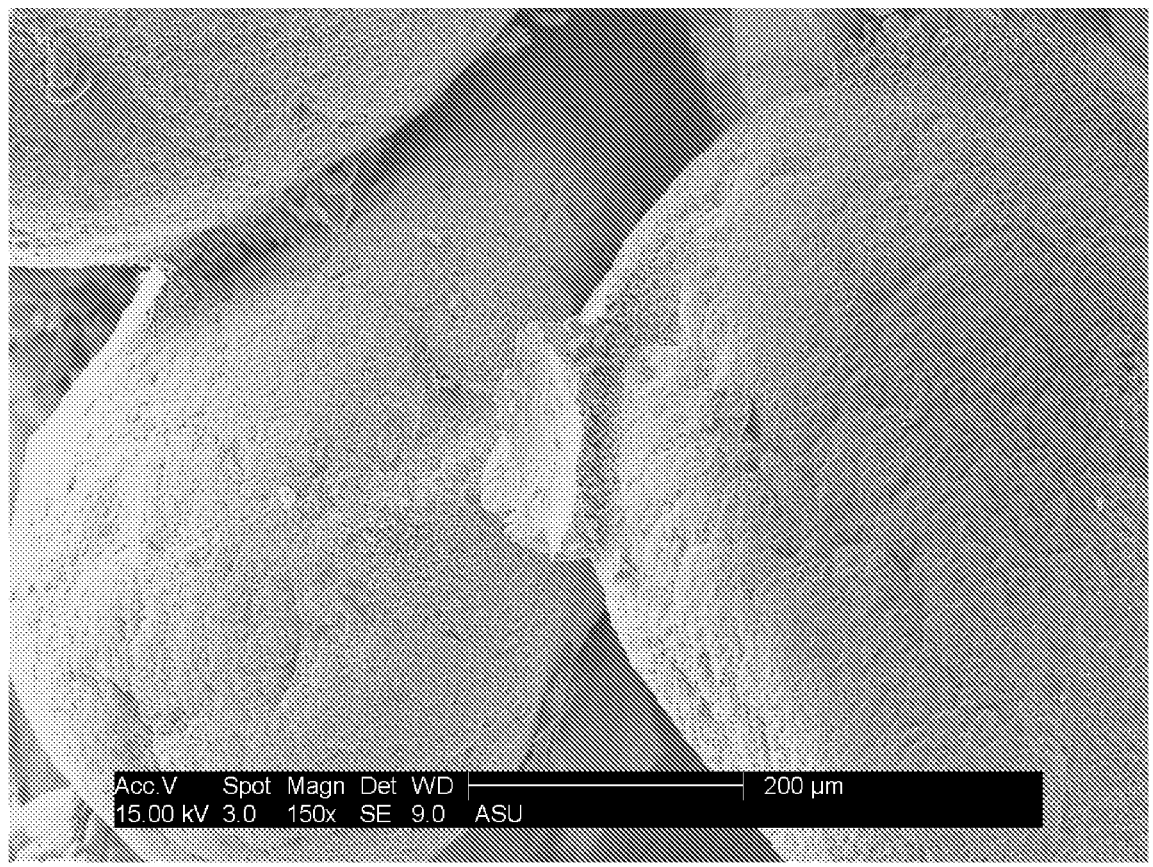
FIG. 8. Image from same mix & compact columns using silica 20-30 as shown in FIG. 7. Note the concave CaCO$_3$ cement where a sand particle was bonded.
Figure 9:
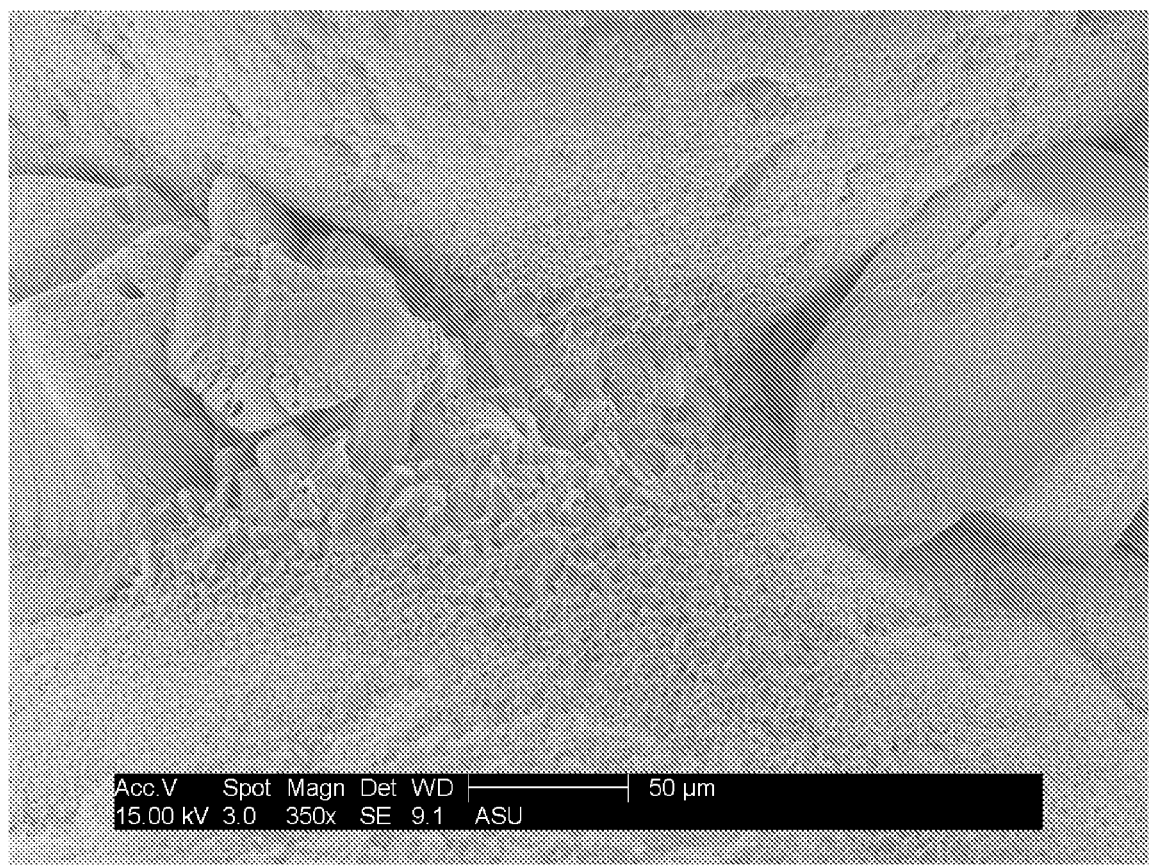
FIG. 9. Image from the same mix & compact columns using silica 20-30 as shown in FIG. 7. These are silica sand particles covered with a growing CaCO$_3$ layer that forms cement at the inter-particle contact. The large particles to the left appear to be well-developed CaCO and possibly evaporates (far left).
Figure 10:
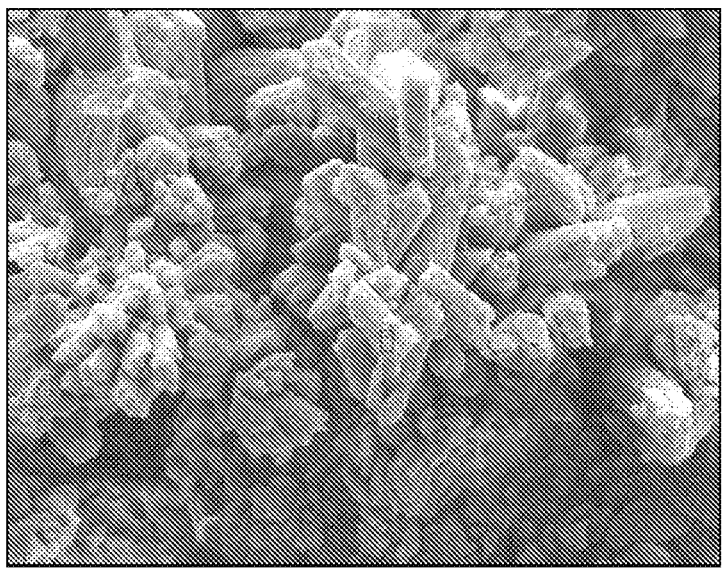
FIG. 10. Low-resolution image from a 4"×12" PVC column #2 using silica 20-30 with bentonite; note the scale (10 μm). These are growing CaCO$_3$ crystals covering silica sand particles (not seen). The CaCO$_3$ is randomly covered or associated with clumps of bentonite, which may be serving as points of nucleation.
Figure 11:
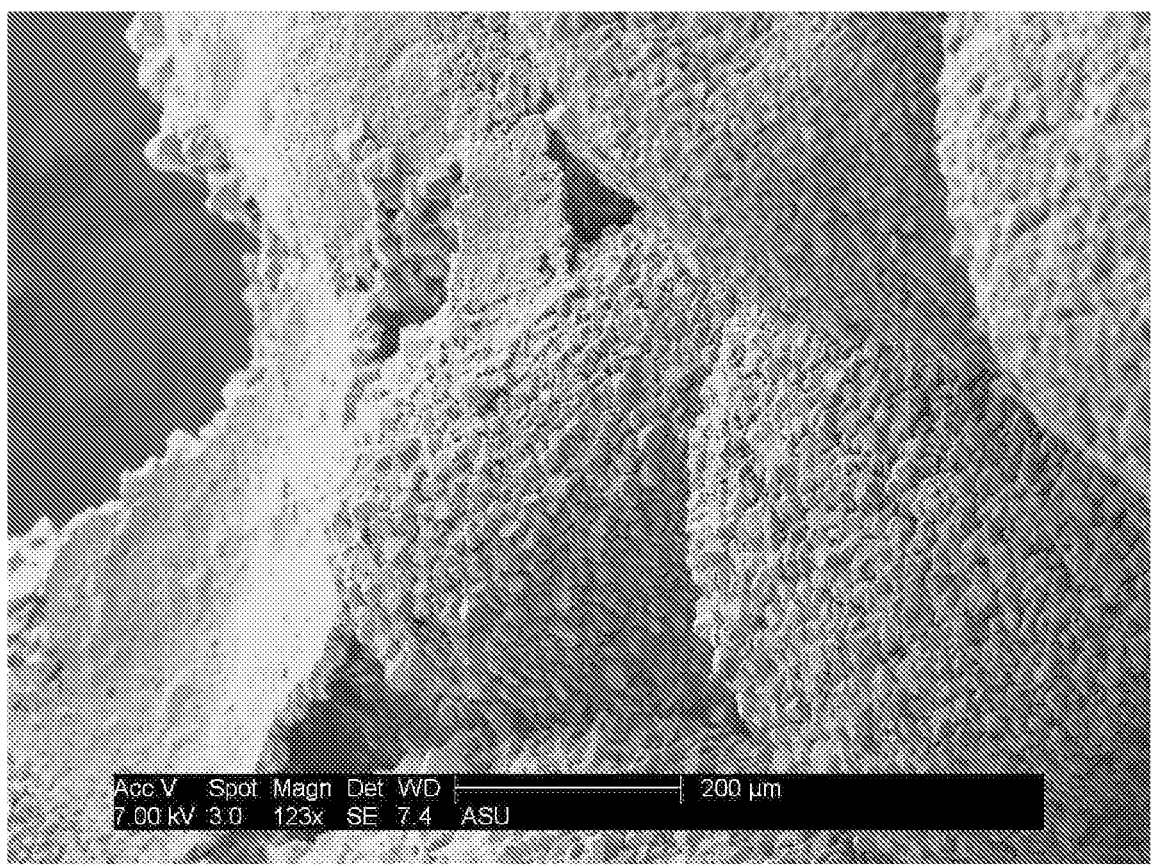
FIG. 11. Image from the 4"×12" PVC column #1 using silica 20-30. These are growing CaCO$_3$ crystals covering silica sand particles. The relatively smooth concave feature is an inter-particle cementation contact.
Figure 12:
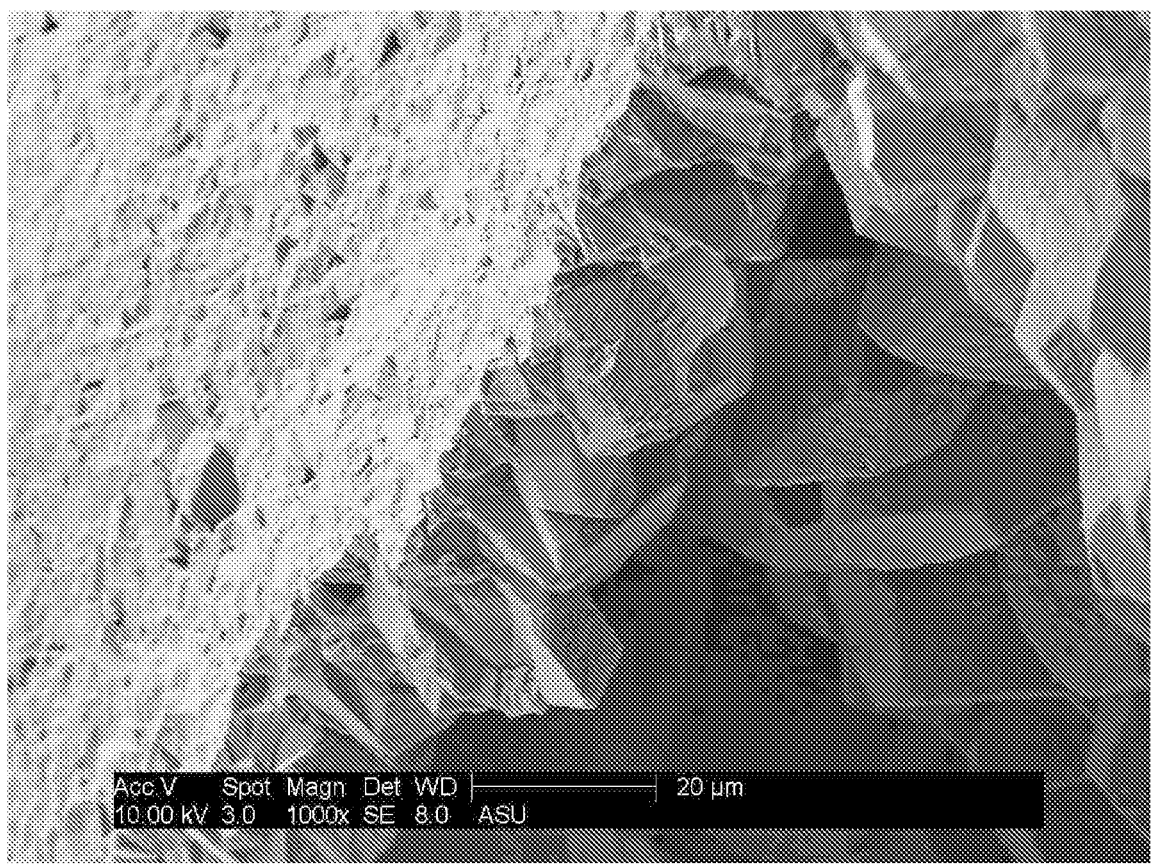
FIG. 12. Image from the same 4"×12" PVC column #1 using silica 20-30 as FIG. 11, but zoomed-in to the relatively smooth concave inter-particle feature described above; these are CaCO$_3$ crystals covering silica sand particles.
Figure 13:
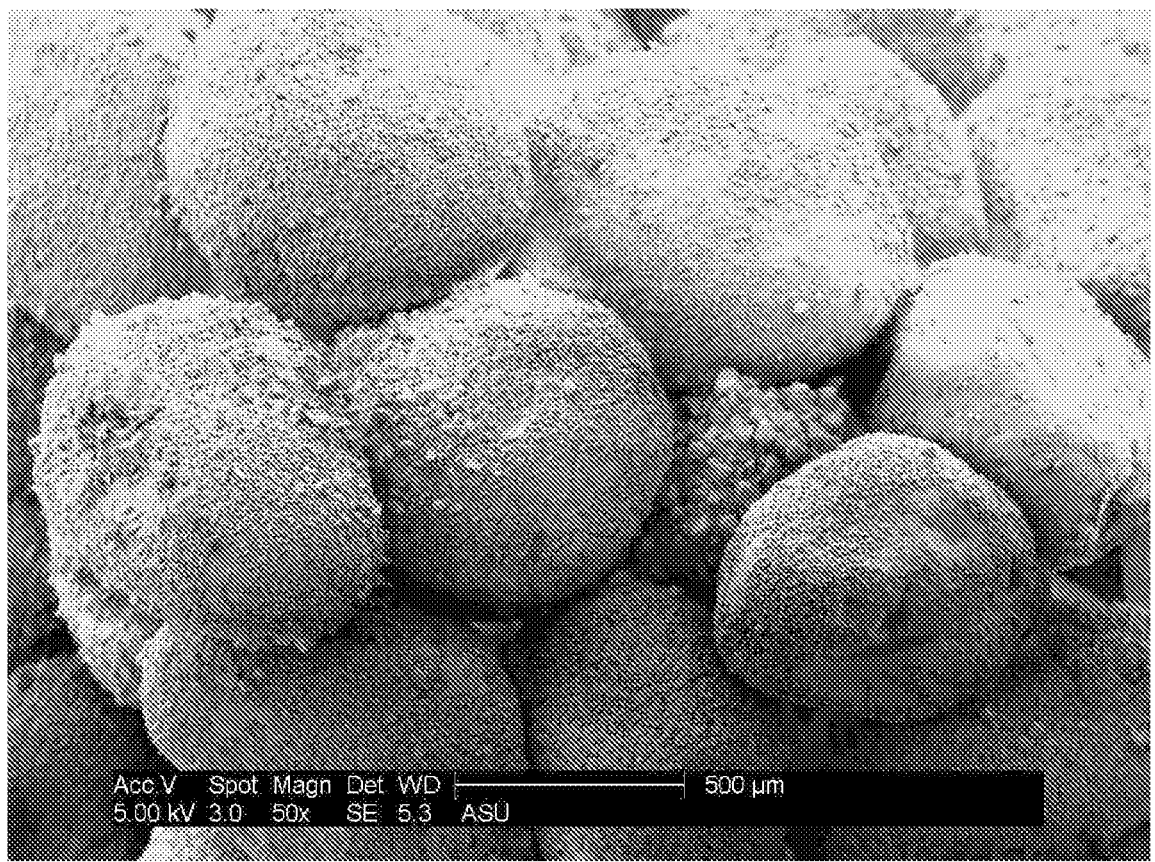
FIG. 13. Image from the same 4"×12" PVC column #1 using silica. 20-30 as in FIG. 11. These are CaCO$_3$ crystals covering silica sand particles.
Figure 14:
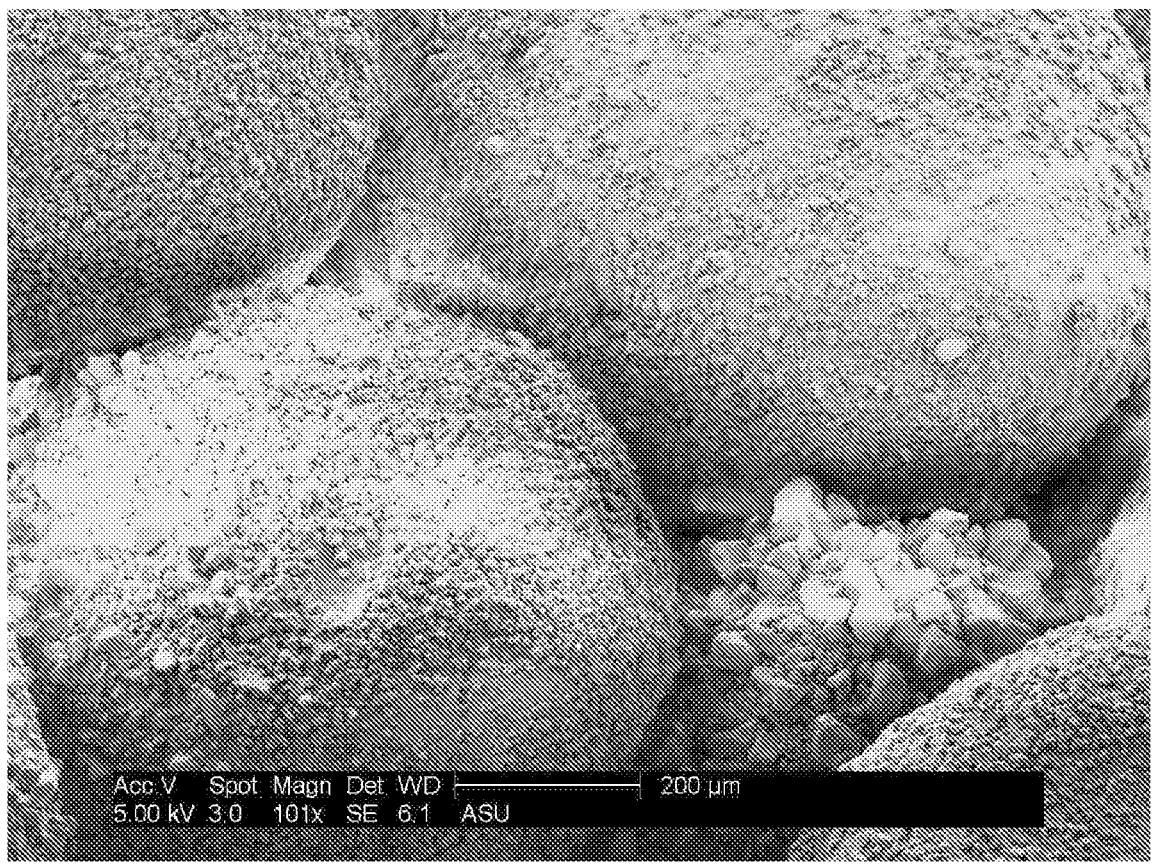
FIG. 14. Image from the same 4"×12" PVC column #1 using; silica 20-30 as in FIG. 11.
Figure 15:
FIG. 15. Image from the 4"×12" PVC column #3 using silica F-60. These are silica sand particles variously covered with CaCO$_3$ crystals.
Figure 16:
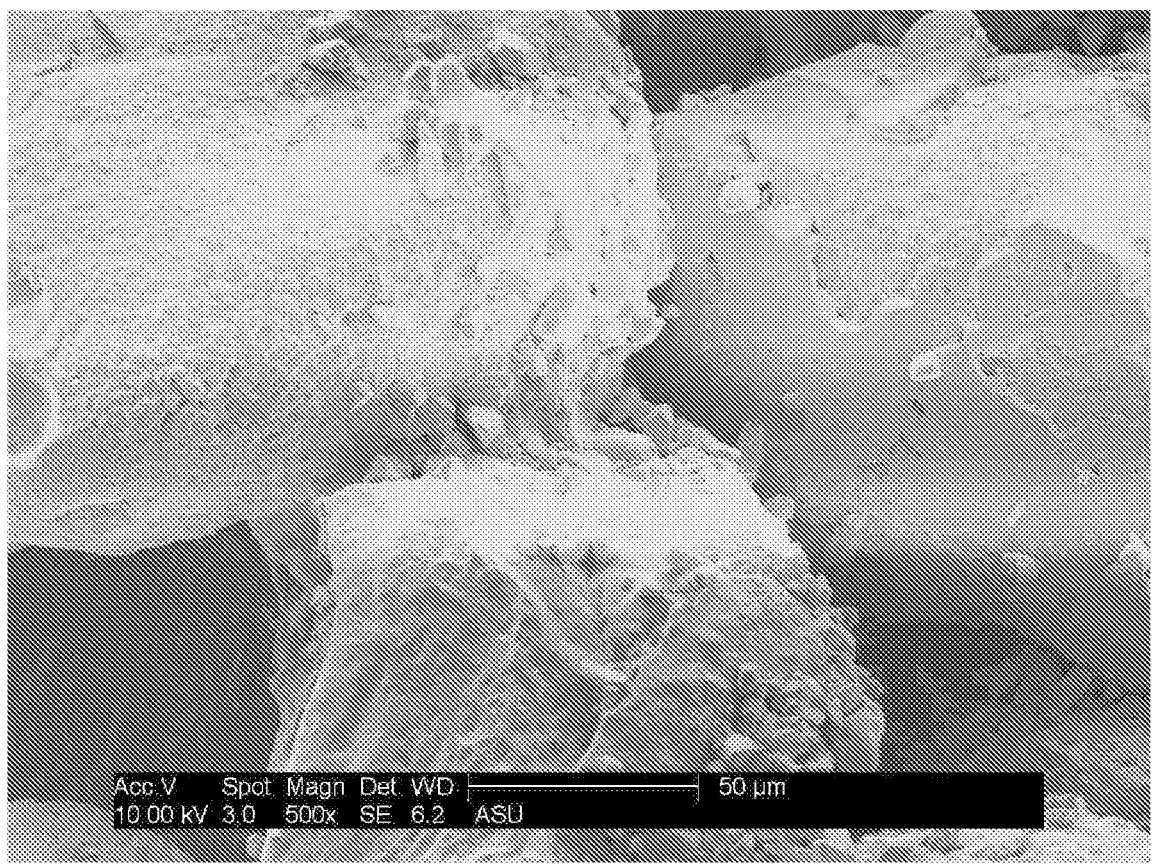
FIG. 16. Image from the same 4"×12" PVC column #3 using silica F-60 as in FIG. 15, but at higher magnification. Note the inter-particle cementation.
Figure 17:
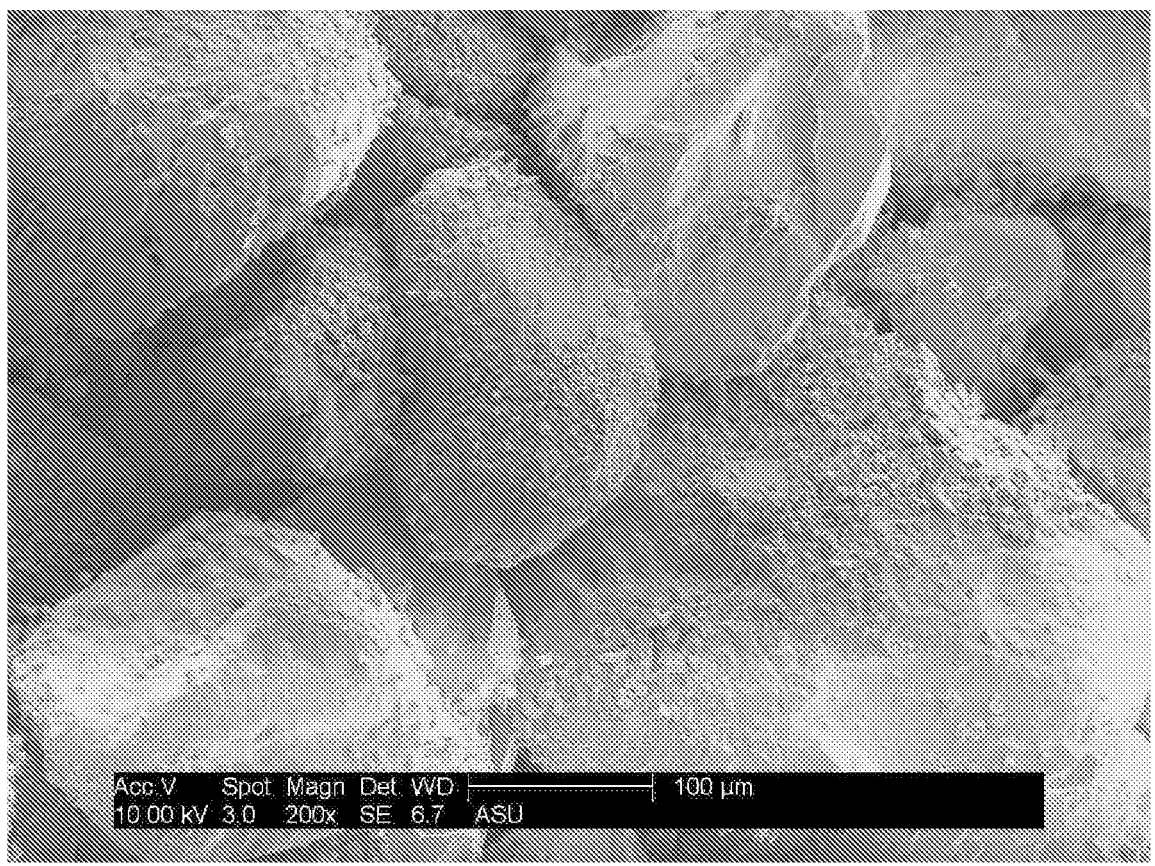
FIG. 17. Image from the same 4"×12" PVC column #3 using silica F-60 as in FIG. 15, but showing different location. These are silica sand particles covered with CaCO$_3$ crystals.
Figure 18:
FIG. 18. Image from the same 4"×12" PVC column #3 using silica F-60 as in FIG. 15, but at higher magnification. These are silica sand particles covered with CaCO$_3$ crystals.
Figure 19:
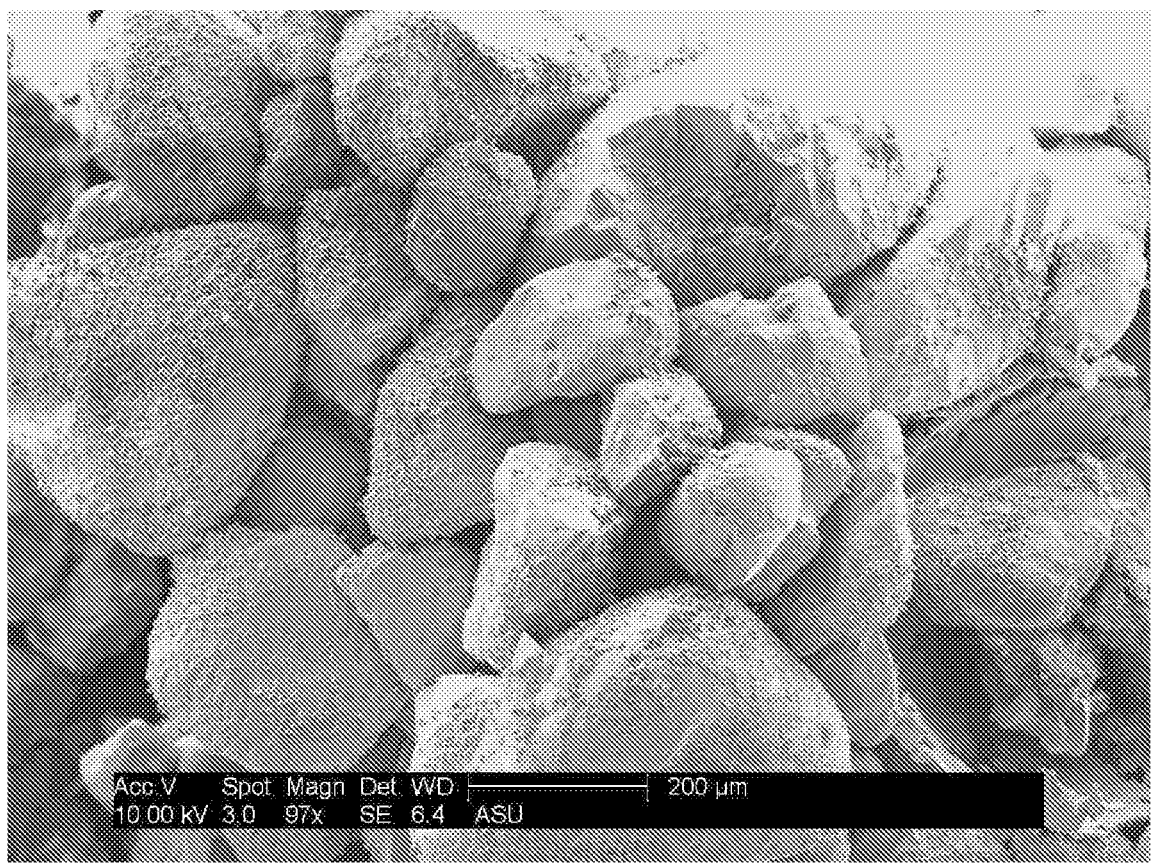
FIG. 19. Image from the same 4"×12" PVC column #3 using silica F-60 as in FIG. 15, but at lower magnification. These are silica sand particles covered with CaCO$_3$ crystals.

Column #3 (F-60 fine sand)—A region of strongly cemented soil began ≈3" from the column bottom, was ≈2.5" in length and displayed a clear bell-shaped top and a flat surface at the bottom. Overall, the cemented region appeared bell-shaped (FIG. 6). The entire soil column was dislodged upon disassembly and many chunks of cemented soil were dislodged to access the most strongly cemented region which had the injection tube firmly embedded. In addition, the soil overall mass contained many small (1-3 mm) pieces of cemented sand. The column had a strong smell of ammonia and displayed significant amounts of gas bubbles during washing.

Example 2 demonstrates (for example) the ability to create roughly cylindrical columns in a saturated soil (i.e. below the water table); stabilize a fine grained material; and the optional facilitation of cementation by first injecting a bentonite slurry into the column, which provides particular benefit when used with more porous (coarser) starting materials.

EXAMPLE 3

In one experiment, using 4" by 12" PVC columns, a final step was used as follows: the injection of approximately 0.01% by volume (~2 ml/column) of pH=13 NaOH during the last week of the experiment. The purpose of this injection was to help drive a shift of ammonium→ammonia to limit the potential of reaction reversal due to the ammonium (this will temporarily increase pH near the point of injection, which is also has a beneficial effect with respect to inducing carbonate precipitation)—this not only limits the potential for reversal of and enhances carbonate precipitation, but also helps rid the system of toxic ammonium salt by-products. A further effect of adding this strong base (NaOH) to the system is that it may help expose/dissolve some of the soil particle or substances clothing the soil particle and thereby facilitate more and/or stronger bonding of the soil to be improved (e.g. gravel, sand, or silt particles susceptible to degradation/dissolution via base) with the precipitated calcite (calcium carbonate).

EXAMPLE 4

Columnar EICP Stabilization Tests

The details of chemical and enzyme preparation are the same as those described in the previous examples, as is the application to different soil types. Test were set-up in 5-gallon buckets using coarse sand. Perforated PVC tubes were placed in center of 5-gal buckets. Buckets then filled w/coarse silica sand; half were wet studies (the soil was essentially saturated, i.e. there was water to almost the top of the soil layer at the start of the experiment) and half were dry studies (i.e.: dry soil). The wet tests simulate improving soil below the water table while the dry test simulates soil above the water table.

Figure 20:
FIG. 20. An image from a columnar EICP study using dry sand injected with cementation solution FIG. 21. An image from a columnar EICP study using wet sand injected with cementation solution
Figure 21:
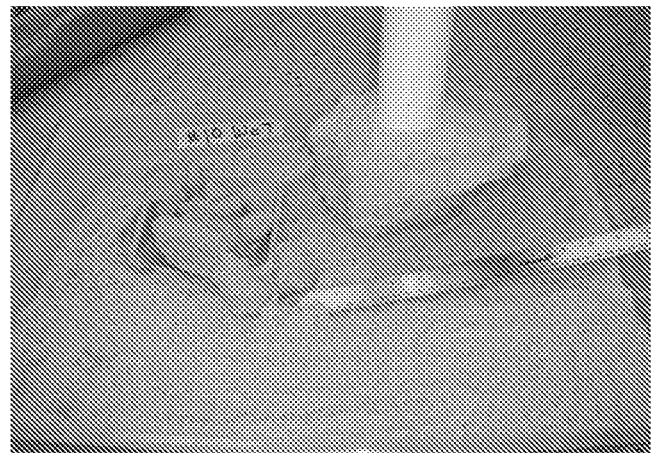

Cementation solution (same conditions as disclosed above) was poured into the perforated PVC tubes. Approximately 3.5 weeks later, 0.1% NaOH (1M) added and the mix was allowed to sit for approximately 2 weeks. The buckets were than rinsed & drained and allowed to sit for approximately 1 week. Cemented soil specimens were then removed from the buckets for analysis. See FIGS. 20-22. The soil stuck to the tubes in all experiments (wet or dry), while the strength of attachment varied from firmly stuck to weakly stuck based on the extent of cementation near the tube. In general, the larger and more uniform the cemented specimen, the more likely to be stuck to the injection tube; similarly, cementation in wet soil generally resulted in some of the cemented specimen being stuck to the injection tube. Penetration of the cementation solution into the dry soil was somewhat more uniform in the wet soil. These data demonstrate effective cementation both wet and dry soil. These data demonstrated that the addition of base (1) resulted in a shift towards $1111_1$ and away from $NH_4^+$, (2) inhibited nitrification, and (3) shifted the $CaCO_3$ reaction towards further precipitation.

We claim:

1. A cementation method, comprising:
(a) combining sand with
   (i) agriculturally-derived urease;
   (ii) urea; and
   (iii) calcium ions;
wherein (i), (ii), (and (iii) are provided in amounts effective and the combining is carried out under conditions suitable to cause carbonate mineral precipitation of the sand to produce a starting material complex, and wherein the combining comprises:
   mixing the agriculturally-derived urease with the sand; and
   injecting into the sand, under pressure and via an injection tube, a solution comprising the urea and the calcium ions into the mixture of sand and agriculturally-derived urease;
(b) utilizing powdered milk as a stabilizer; and
(c) injecting into the starting material complex, under pressure and via an injection tube, Ca(OH)$_2$ under conditions to mitigate formation of ammonium salts in the starting material complex.

2. The method of claim 1, wherein the Ca(OH)$_2$ is injected under pressure into the starting material complex at a plurality of locations.

3. The method of claim 1, wherein the pH of the starting material complex increases where the starting material complex contacts the Ca(OH)$_2$.

4. The method of claim 1, wherein the method is used for improving bearing capacity of a building foundation.

5. The method of claim 1, wherein the combining is conducted underneath or adjacent to an existing structure that is sensitive to ground settlement or heave.

6. The method of claim 5, wherein the carbonate mineral precipitation does not cause ground settlement or heave affecting the existing structure.

7. The method of claim 6, wherein step (a), step (h), and step (c) are carried out in situ without disturbing the sand.

8. The method of claim 1, wherein the injection tube comprises a perforated pipe.

9. The method of claim 1, further comprising introducing a clay slurry into the sand prior to or concurrent with combining the sand with the agriculturally-derived urease, the urea, and the calcium ions.

10. The method of claim 1, wherein the sand is configured in a column beneath a residential structure, wherein the injecting provides mitigation of earthquake-induced liquefaction damage to the structure, wherein the column has a diameter of between 0.3 meters and 1.5 meters, and wherein the column has a length of less than 20 meters.

11. The method of claim 1, wherein the sand is saturated with water.

12. The method of claim 1, wherein the sand is not part of an oil-bearing formation.

13. The method of claim 1, wherein the performing step (a), step (b), and step (c) results in a reduced liquefaction potential of the sand.

* * * * *